US011242565B2

(12) United States Patent
Tan et al.

(10) Patent No.: US 11,242,565 B2
(45) Date of Patent: Feb. 8, 2022

(54) MULTIGENE ASSAY

(71) Applicant: LUCENCE LIFE SCIENCES PTE LTD, Singapore (SG)

(72) Inventors: Min-Han Tan, Singapore (SG); Puay Hoon Tan, Singapore (SG); Wai Jin Tan, Singapore (SG); Igor Cima, Singapore (SG)

(73) Assignee: LUCENCE LIFE SCIENCES PTE LTD., Singapore (SG)

( * ) Notice: Subject to any disclaimer, the term of this patent is extended or adjusted under 35 U.S.C. 154(b) by 1081 days.

(21) Appl. No.: 15/557,776

(22) PCT Filed: Mar. 14, 2016

(86) PCT No.: PCT/SG2016/050117
§ 371 (c)(1),
(2) Date: Sep. 12, 2017

(87) PCT Pub. No.: WO2016/144267
PCT Pub. Date: Sep. 15, 2016

(65) Prior Publication Data
US 2018/0073083 A1  Mar. 15, 2018

(30) Foreign Application Priority Data
Mar. 12, 2015 (SG) .............................. 10201501928T

(51) Int. Cl.
*C12Q 1/6886* (2018.01)
*G16H 50/30* (2018.01)
*G16H 10/40* (2018.01)
*G16H 20/00* (2018.01)
*G16B 25/10* (2019.01)
*C12Q 1/686* (2018.01)

(52) U.S. Cl.
CPC ........... *C12Q 1/6886* (2013.01); *C12Q 1/686* (2013.01); *G16B 25/10* (2019.02); *G16H 10/40* (2018.01); *G16H 20/00* (2018.01); *G16H 50/30* (2018.01); *C12Q 2545/00* (2013.01); *C12Q 2600/106* (2013.01); *C12Q 2600/112* (2013.01); *C12Q 2600/158* (2013.01); *G01N 2800/52* (2013.01)

(58) Field of Classification Search
None
See application file for complete search history.

(56) References Cited

FOREIGN PATENT DOCUMENTS

| EP | 2 669 682 A1 | 12/2013 |
|---|---|---|
| WO | WO 2008/132167 A2 | 11/2008 |
| WO | WO 2013/075059 A1 | 5/2013 |

OTHER PUBLICATIONS

Lossos et al. Optimization of quantitative real-time RT-PCR parameters for the study of lymphoid malignancies Leukemia vol. 17, pp. 789-795 (Year: 2003).*
Vandesompele et al. Accurate normalization of real-time quantitative RT-PCR data by geometric averaging of multiple internal control genes Genome Biology vol. 3 pp. research0034.1-0034.11 (Year: 2002).*
Bieche et al. Quantitation of MYC Gene Expression in Sporadic Breast Tumors with a Real-Time Reverse Transcription-PCR Assay Cancer Research vol. 59, pp. 2759-2765 (Year: 1999).*
Ai et al. TRIM29 Suppresses TWIST1 and Invasive Breast Cancer Behavior Cancer Research vol. 74 pp. 4875-4887 (Year: 2014).*
Spitaleri et al. Breast phyllodes tumor: A review of literature and a single center retrospective series analysis Critical Reviews in Oncology/Hematology vol. 88, pp. 427-436 (Year: 2013).*
Tan P. H.; et al.; "Predicting clinical behaviour of breast phyllodes tumours: a nomogram based on histological criteria and surgical margins"; J Clin Pathol 65: 69-76 (2012); 9 pp.
PCT International Search Report for PCT Counterpart Application No. PCT/SG2016/050177, 7 pgs. (dated May 13, 2016).
PCT Written Opinion for PCT Counterpart Application No. PCT/SG2016/050117, 7 pgs. (dated May 13, 2016).
PCT International Preliminary Report on Patentability for PCT Application No. PCT/SG2016/050117, 19 pgs. (dated Jan. 25, 2017).
Arno Kuijper, "Pathogenesis and progression of fibroepithelial breast tumors," Utrecht University Repository, 192 pages (Jul. 13, 2006).
Maria Vidal, et al., "Gene expression-based classifications of fibroadenomas and phyllodes tumours of the breast," Molecular Oncology, vol. 9, Issue 6, pp. 1081-1090 (Jun. 2015).

(Continued)

*Primary Examiner* — John S Brusca
(74) *Attorney, Agent, or Firm* — Womble Bond Dickinson (US) LLP

(57) ABSTRACT

An in vitro method of determining the type of a fibroepithelial tumour of the breast in a biological sample is provided. The method comprises the steps of obtaining an expression profile of one or more genes selected from the group consisting of PRAME, ADH1 B, CTHRC1, NPTX2, NEFL, ABCA8, DAPL1, TP63_v2, COL17A1, GCNT2, CCL19, MMP3, FN1, TRERF1, TRIM29, TESC, KIF20A, UHRF1, HEPACAM2, APOD, SERHL2. KIF15, HOXD13, GAGE2B, CALML5, C2orf40, ADH1C, CYP1B1, SPAG11B, GRB7, UBE2C, SYNGAP1, TP63_v1, LAMB1, OR5P3, SPC25, SHISA2, SCARA5, LHX2, RORC, DPYSL4, CH25H, and CHST1 in a sample and determining the differential activity of the one or more genes relative to a control; correlating the differential activity of the one or more genes relative to the control to obtain a p-score; and determining the type of fibroepithelial tumour based on the p-score, wherein a p-score of less than 0.5 is indicative of a fibroadenoma and a p-score of 0.5 and above is indicative of phyllodes tumour. Particularly, the said method is exemplified using an expression profile of five genes comprising of PRAME, FN1, CCL19, ABCA8 and APOD. A method for managing the treatment of a subject with a fibroepithelial tumour of the breast is also provided as well as a kit when used in the methods of the present invention.

13 Claims, 3 Drawing Sheets

Specification includes a Sequence Listing.

(56) References Cited

OTHER PUBLICATIONS

A Sapino, et al., "Estrogen receptor-[beta]is expressed in stromal cells of fibroadenoma and phyllodes tumors of the breast," Modern Pathology, vol. 19, pp. 599-606 (Apr. 2006).
Ashley Cimino-Mathews, et al., "A subset of malignant phyllodes tumors express p63 and p40: a diagnostic pitfall in breast core needles biopsies," Am J Surg Pathol., vol. 38, No. 12, pp. 1689-1696 (Dec. 2014).
Yup Kang, et al., "Expression of anaphase-promoting complex7 in fibro adenomas and phyllodes tumors of breast," Human Pathology, vol. 40, Issue 1, pp. 98-107 (Jan. 2009).
Yijun Sun, et al., "Derivation of molecular signatures for breast cancer recurrence prediction using two-way validation approach," Breast Cancer Res Treat., vol. 119, No. 3, pp. 593-599 (Feb. 2010).
MT Epping, et al., "PRAME expression and clinical outcome of breast cancer," British Journal of Cancer, vol. 99, No. 3, pp. 398-403 (Aug. 5, 2008).
JL Huan, et al., "Screening for key genes associated with invasive ductal carcinoma of the breast via microarray data analysis," Genetics and Molecular Research, vol. 13, No. 3, pp. 7919-7925 (Sep. 29, 2014).
Antonella De Luca, et al., "RNA-seq analysis reveals significant effects of EGFR signaling on the secretome of mesenchymal stem cells," Oncotarget, vol. 5, No. 21, pp. 10518-10528 Nov. 2014).
Therese Sorlie, et al. "Gene expression patterns of breast carcinomas distinguish tumor subclasses with clinical implications," PNAS, vol. 95, No. 19, pp. 10859-10874 (Sep. 11, 2001).
Xiaobo Zhou, et al., "Cancer classification and prediction using logistic regression with Bayesian gene selection," Journal of Biomedical Informatics, vol. 37, Issue 4, pp. 249-259 (Aug. 2004).
Wai Jin Tan, et al., "A five-gene reverse transcription-PCR assay for pre-operative classification of breast fibroephithella lesions," Breast Cancer Research, vol. 15, No. 31 (Mar. 9, 2016).
The Supplementary Examination Report for Singaporean Application No. 11201707067U dated Feb. 17, 2021, 3 pages.
The Office Action for Chinese Application No. 201680027180X dated Oct. 20, 2020, 15 pages.
The Transmission of the certificate for a European Patent for European Application No. 16762079.8 dated Jul. 27, 2020, 2 pages.
The Decision to Grant for European Application No. 16762079.8 dated Jun. 18, 2020, 2 pages.
Sklair-Levy et al., "Incidence and Management of Complex Fibroadenomas", American Journal of Roentgenology. Jan. 2008; vol. 190, pp. 214-218.

\* cited by examiner

MULTIGENE ASSAY

CROSS-REFERENCE TO RELATED APPLICATIONS

This patent application is a U.S. National Phase Application under 35 U.S.C. § 371 of International Application No. PCT/SG2016/050117, filed on 14 Mar. 2016, entitled A MULTIGENE ASSAY, which claims the benefit of priority of Singapore provisional application No. 10201501928T, filed 12 Mar. 2015, the contents of which were incorporated by reference in its entirety for all purposes.

INCORPORATION BY REFERENCE

This patent application incorporates by reference the material (i.e., Sequence Listing) in the ASCII text file named 9869sg3698_ST25_1790974_1_1824268_1.txt, created on Sep. 12, 2017, having a file size of 20,480 bytes.

FIELD OF THE INVENTION

The present invention relates to assays for tumours of the breast and in particular, assays for differentiating benign and malignant fibroepithelial tumours of the breast. More specifically, the present invention relates to multigene assays using samples obtained by biopsy or excision and methods for managing the treatment of a subject with a fibroepithelial tumour of the breast. Kits of reagents are also provided.

BACKGROUND OF THE INVENTION

Fibroepithelial tumours are biphasic tumours that consist of epithelial and stromal tissue. In the breast, fibroepithelial tumours represent a heterogeneous group of tumours that range from benign to malignant. Of these, fibroadenomas account for a large percentage of benign fibroepithelial tumours, while phyllodes tumours (PT) range from benign to malignant and have unpredictable clinical outcomes.

The heterogeneous nature of fibroepithelial tumours equates to a wide range of clinical and pathological features. Accordingly, distinction between fibroadenomas and PTs is important in order to guide the surgical decision for margin width during resection of breast tumours and for appropriate clinical management.

However, it is not always possible to definitively diagnose fibroadenomas from PTs. Fibroadenomas and PTs share some overlapping morphology, and biopsy or excision material for diagnosis may be limited. Furthermore, morphologic predictors of malignancy such as mitotic activity, infiltrative borders, tumour necrosis, positive margins and tumour size are not definitive markers of malignancy.

There is therefore a need for a method to differentiate fibroadenomas and PTs that allows definitive diagnosis of a PT, which would in turn guide clinical management of the patient.

SUMMARY OF THE INVENTION

In one aspect, there is provided a method of determining a fibroepithelial tumour of the breast, in a biological sample in vitro, comprising: obtaining an expression profile of one or more genes selected from the group consisting of PRAME, ADH1B, CTHRC1, NPTX2, NEFL, ABCA8, DAPL1, TP63_v2, COL17A1, GCNT2, CCL19, MMP3, FN1, TRERF1, TRIM29, TESC, KIF20A, UHRF1, HEPACAM2, APOD, SERHL2, KIF15, HOXD13, GAGE2B, CALML5, C2orf40, ADH1C, CYP1B1, SPAG11B, GRB7, UBE2C, SYNGAP1, TP63_v1, LAMB1, OR5P3, SPC25, SHISA2, SCARA5, LHX2, RORC, DPYSL4, CH25H, and CHST1, in said sample;

obtaining an expression profile of one or more normalized genes for use as a control;

determining the differential activity of the one or more genes relative to the control based on the expression profile of the one or more genes and one or more normalized genes;

correlating the differential activity of the one or more genes relative to the control to obtain a p-score; and determining the type of fibroepithelial tumour based on the p-score, wherein a p-score of less than 0.5 is indicative of a fibroadenoma and a p-score of 0.5 and above is indicative of phyllodes tumour.

In one aspect, there is provided a method for managing the treatment of a subject with a fibroepithelial tumour of the breast, comprising:

obtaining an expression profile of one or more genes selected from the group consisting of PRAME, ADH1B, CTHRC1, NPTX2, NEFL, ABCA8, DAPL1, TP63_v2, COL17A1, GCNT2, CCL19, MMP3, FN1, TRERF1, TRIM29, TESC, KIF20A, UHRF1, HEPACAM2, APOD, SERHL2, KIF15, HOXD13, GAGE2B, CALML5, C2orf40, ADH1C, CYP1B1, SPAG11B, GRB7, UBE2C, SYNGAP1, TP63_v1, LAMB1, OR5P3, SPC25, SHISA2, SCARA5, LHX2, RORC, DPYSL4, CH25H, and CHST1, in a biological sample obtained from the subject;

obtaining an expression profile of one or more normalized genes for use as a control;

determining the differential activity of the one or more genes relative to the control based on the expression profile of the one or more genes and one or more normalized genes;

correlating the differential activity of the one or more genes relative to the control to obtain a p-score;

determining the type of fibroepithelial tumour based on the p-score, wherein a p-score of less than 0.5 is indicative of fibroadenoma and a p-score of 0.5 and above is indicative of phyllodes tumour; and selecting the treatment of the patient based upon the type of fibroepithelial tumour and p-score.

In one aspect, there is provided a kit when used in the method as described herein, comprising:

a primer pair for amplifying the one or more genes selected from the group consisting of PRAME, ADH1B, CTHRC1, NPTX2, NEFL, ABCA8, DAPL1, TP63_v2, COL17A1, GCNT2, CCL19, MMP3, FN1, TRERF1, TRIM29, TESC, KIF20A, UHRF1, HEPACAM2, APOD, SERHL2, KIF15, HOXD13, GAGE2B, CALML5, C2orf40, ADH1C, CYP1B1, SPAG11B, GRB7, UBE2C, SYNGAP1, TP63_v1, LAMB1, OR5P3, SPC25, SHISA2, SCARA5, LHX2, RORC, DPYSL4, CH25H, and CHST1.

In one aspect, there is provided a method of determining the type of fibroepithelial tumour of the breast in a biological sample in vitro, comprising:

obtaining an expression profile of a combination of genes comprising PRAME, ABCA8, CCL19 FN1 and APOD in said sample;

obtaining an expression profile of one or more normalized genes for use as a control;

determining the differential activity of PRAME, ABCA8, CCL19, FN1 and APOD relative to the control based on the expression profile of the one or more genes and one or more normalized genes;

correlating the differential activity of PRAME, ABCA8, CCL19, FN1 and APOD relative to the control to obtain a p-score usin a predictive algorithm, wherein the predictive algorithm is:

$$p = \frac{e^{2.95575(\Delta Ct\ of\ APOD) - 0.11934(\Delta Ct\ of\ APOD*\Delta Ct\ of\ ABCA8) - 0.43165(\Delta Ct\ of\ PRAME*\Delta Ct\ of\ FN1) + 0.08326(\Delta Ct\ of\ PRAME*\Delta Ct\ of\ CCL19)}}{1 + e^{2.95575(\Delta Ct\ of\ APOD) - 0.11934(\Delta Ct\ of\ APOD*\Delta Ct\ of\ ABCA8) - 0.43165(\Delta Ct\ of\ PRAME*\Delta Ct\ of\ FN1) + 0.08326(\Delta Ct\ of\ PRAME*\Delta Ct\ of\ CCL19)}};$$

and
determining the type of fibroepithelial tumour based on the p-score, wherein a p-score of less than 0.5 is indicative of a fibroadenoma and a p-score of 0.5 and above is indicative of phyllodes tumour.

In one aspect, there is provided a method for managing the treatment of a subject with a fibroepithelial tumour of the breast, comprising:
obtaining an expression profile of a combination of genes comprising PRAME, ABCA8, CCL19, FN1 and APOD, in a biological sample obtained from the subject;
obtaining an expression profile of one or more normalized genes for use as a control;
determining the differential activity of PRAME, ABCA8, CCL19, FN1 and APOD relative to the control based on the expression profile of the one or more genes and one or more normalized genes;
correlating the differential activity of PRAME, ABCA8, CCL19, FN1 and APOD relative to the control to obtain a p-score using a predictive algorithm, wherein the predictive algorithm is:

$$p = \frac{e^{2.95575(\Delta Ct\ of\ APOD) - 0.11934(\Delta Ct\ of\ APOD*\Delta Ct\ of\ ABCA8) - 0.43165(\Delta Ct\ of\ PRAME*\Delta Ct\ of\ FN1) + 0.08326(\Delta Ct\ of\ PRAME*\Delta Ct\ of\ CCL19)}}{1 + e^{2.95575(\Delta Ct\ of\ APOD) - 0.11934(\Delta Ct\ of\ APOD*\Delta Ct\ of\ ABCA8) - 0.43165(\Delta Ct\ of\ PRAME*\Delta Ct\ of\ FN1) + 0.08326(\Delta Ct\ of\ PRAME*\Delta Ct\ of\ CCL19)}};$$

determining the type of fibroepithelial tumour based on the p-score, wherein a p-score of less than 0.5 is indicative of fibroadenoma and a p-score of 0.5 and above is indicative of phyllodes tumour; and
selecting the treatment of the patient based upon the type of fibroepithelial tumour and p-score.

In one aspect, there is provided a kit when used in the method as disclosed herein comprising:
a primer pair for amplifying the combination of genes comprising PRAME ABCA8, CCL19, FN1 and APOD.

Definitions

The terms "biological material" or "biological sample" as used herein refers to any material or sample, which includes an analyte as defined herein. Such samples may, for example, include samples derived from or comprising stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, for example, from all suitable organs, for example, the lung, the muscle, brain, breast, liver, skin, pancreas, stomach, etc., a nucleated cell sample, a fluid associated with a mucosal surface, hair, or skin.

The term "polymerase chain reaction (PCR)" refers to an enzyme-mediated reaction use to amplify a specific target DNA sequence. By amplifying the target DNA sequence in the DNA template, it is then able to produce millions more copies of the targeted DNA sequence. This is useful when a biological sample contains only small amounts of DNA. PCR is carried out in a mixture containing DNA polymerase, a pair of primers (forward and reverse) and four deoxynucleotide triphosphates (dNTPs) with the aid of thermal cycler. A PCR reaction cycle typically involves a denaturation step to yield single stranded DNA molecules, an annealing step to allow primers to anneal to the DNA molecules, an extension/elongation step to allow a new complementary strand of DNA to be synthesized. The PCR reaction cycle is repeated to allow amplification of the target DNA.

The term "cycle threshold" or "Ct" as used herein refers to the number of cycles of a PCR reaction cycle that is required before a target DNA is positively detected. Ct levels are inversely proportional to the amount of target DNA in a sample.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF THE PRESENT INVENTION

Figure 1:
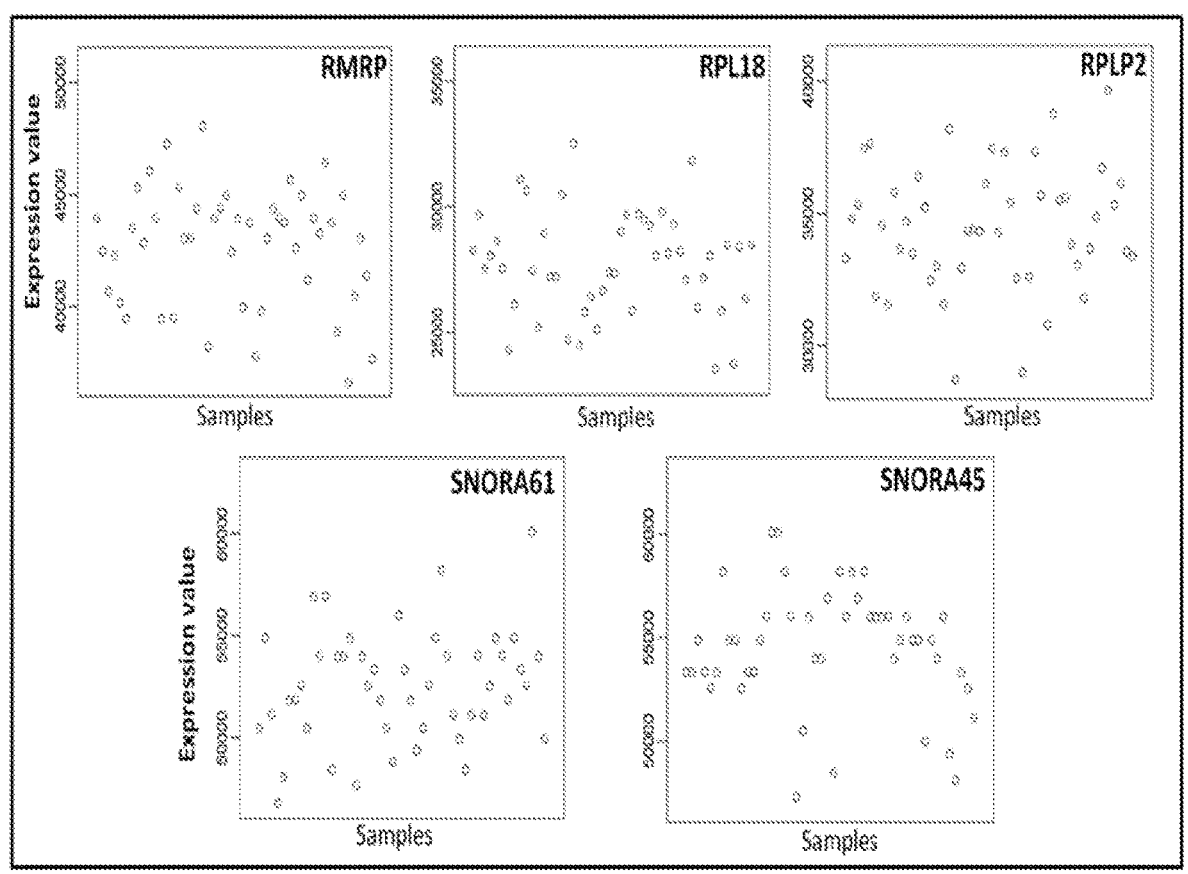
FIG. 1. Expression value of the five genes selected for normalization in 48 samples. Five genes with the least variable expression in 48 samples were selected for normalization. The genes selected were RMRP, RPL18, RPLP2, SNORA61 and SNORA45.

In a first aspect the present invention refers to a method of method of determining a fibroepithelial tumour of the breast, in a biological sample in vitro. The method may comprise: obtaining an expression profile of one or more genes selected from the group consisting of PRAME, ADH1B, CTHRC1, NPTX2, NEFL, ABCA8, DAPL1, TP63_v2, COL17A1, GCNT2, CCL19, MMP3, FN1, TRERF1, TRIM29, TESC, KIF20A, UHRF1, HEPACAM2, APOD, SERHL2, KIF15, HOXD13, GAGE2B, CALML5, C2orf40, ADH1C, CYP1B1, SPAG11B, GRB7, UBE2C, SYNGAP1, TP63_v1, LAMB1, OR5P3, SPC25, SHISA2, SCARA5, LHX2, RORC, DPYSL4, CH25H, and CHST1, in said sample; obtaining an expression profile of one or more normalized genes for use as a control; determining the differential activity of the one or more genes relative to the control based on the expression profile of the one or more genes and one or more normalized genes; correlating the differential activity of the one or more genes relative to the control to obtain a p-score; and determining the type of fibroepithelial tumour based on the p-score, wherein a p-score of less than 0.5 is indicative of a fibroadenoma and a p-score of 0.5 and higher is indicative of phyllodes tumour.

The one or more genes may be selected from the group consisting of PRAME, TRIM29, FN1, CCL19, ABCA8, NPTX2 and APOD. In one embodiment, two, three, four or five or more genes may be selected from the group consisting of PRAME, TRIM29, FN1, CCL19, ABCA8, NPTX2 and APOD. In a preferred embodiment, the one or more genes may consist of PRAME, FN1, CCL19, ABCA8, and APOD.

The one or more genes may be compared against one or more reference genes. A reference gene is a gene that is used as a basis of comparison with a gene of interest. It will be understood to one of skill in the art that the expression level of a gene of interest may be normalized against one or more reference genes to obtain an expression level of the gene of interest relative to the reference gene. Normalization of the expression level of a gene of interest against one or more reference genes allows for the comparison of the expression levels of multiple genes of interest within a sample and/or between samples.

A reference gene may be a housekeeping gene or a normalized or normalization gene. One or more reference genes may be used alone or in combination. Housekeeping genes are well known in the art and refer to genes that are constitutively expressed in all cells of an organism under normal physiological conditions. Examples of housekeeping genes include but are not limited to β-actin, GAPDH and 18S. A normalized gene is one that has whose expression varies minimally across all samples. Normalized genes may be selected based on the smallest value of coefficient of variance (mean/standard deviation). A normalized gene may be a housekeeping gene or any other gene whose expression varies minimally across all samples.

In one embodiment, the one or more normalized genes may be selected from the group consisting of RMRP, RPL18, RPLP2, SNORA61 and SNORA45. In a preferred embodiment, the one or more normalized genes may consist of RMRP, RPL18, RPLP2, SNORA61 and SNORA45.

In one embodiment, the step of correlating the differential activity of the one or more genes relative to the control to obtain a p-score comprises calculating a ΔCt (Delta threshold cycle) value for the one or more genes. It will generally be understood that the ΔCt value is the Ct value for a gene normalized to one or more normalized genes. In one example, the ΔCt of a gene to be tested may be the Ct value of the gene, normalized to one or more normalized genes. In a preferred example, the ΔCt of a gene to be tested may be the Ct value of the gene, normalized to the geometric mean (Ct of the five normalized genes) as follows: ΔCt of test gene=Ct of test gene−geometric mean (Ct of five normalization genes)

It will generally be understood that one, two, three, four, five or more normalization genes may be used in the ΔCt calculation.

The ΔCt value may be used to calculate a p-score using a predictive algorithm. For example, a predictive algorithm may be:

$$p = \frac{e^{2.95575(\Delta Ct \text{ of } APOD) - 0.11934(\Delta Ct \text{ of } APOD * \Delta Ct \text{ of } ABCA8) - 0.43165(\Delta Ct \text{ of } PRAME * \Delta Ct \text{ of } FN1) + 0.08326(\Delta Ct \text{ of } PRAME * \Delta Ct \text{ of } CCL19)}}{1 + e^{2.95575(\Delta Ct \text{ of } APOD) - 0.11934(\Delta Ct \text{ of } APOD * \Delta Ct \text{ of } ABCA8) - 0.43165(\Delta Ct \text{ of } PRAME * \Delta Ct \text{ of } FN1) + 0.08326(\Delta Ct \text{ of } PRAME * \Delta Ct \text{ of } CCL19)}}$$

In one embodiment, the biological sample may be selected from the group consisting of an organ, tissue, fraction, and a cell. A tissue sample may be obtained from tumour tissue selected from the group consisting of frozen tissue, tissue biopsies, circulating tumour cells, bodily fluids or other biological sample.

The biological sample may be a fresh, frozen, or fixed sample. In one embodiment, the biological sample may be formalin-fixed and paraffin embedded (FFPE).

In one embodiment, the bodily fluids may be selected from the group consisting of ascites, effusions, cerebrospinal and urine.

In a one embodiment, the biological sample may be a malignant tumour sample. In another embodiment, the biological sample may be a benign tumour sample. In a further preferred embodiment, the tumour sample may be a sample from the breast.

In one embodiment, RNA may be extracted from the biological sample in order to obtain the expression profile of the one or more genes and one or more normalized genes. In another embodiment, the expression profile of the one or more genes and one or more normalized genes is obtained from the sample biological sample. In yet another embodiment, the expression profile of the one or more genes and one or more normalized genes may be obtained by a quantitative PCR method.

In another aspect, the present invention refers to a method for managing the treatment of a subject with a fibroepithelial tumour of the breast. The method may comprise: obtaining an expression profile of one or more genes selected from the group consisting of PRAME, ADH1B, CTHRC1, NPTX2, NEFL, ABCA8, DAPL1, TP63_v2, COL17A1, GCNT2, CCL19, MMP3, FN1, TRERF1, TRIM29, TESC, KIF20A, UHRF1, HEPACAM2, APOD, SERHL2, KIF15, HOXD13, GAGE2B, CALML5, C2orf40, ADH1C, CYP1B1, SPAG11B, GRB7, UBE2C, SYNGAP1, TP63_v1, LAMB1, OR5P3, SPC25, SHISA2, SCARA5, LHX2, RORC, DPYSL4, CH25H, and CHST1, in a biological sample obtained from the subject; obtaining an expression profile of one or more normalized genes for use as a control; determining the differential activity of the one or more genes relative to the control based on the expression profile of the one or more genes and one or more normalized genes; correlating the differential activity of the one or more genes relative to the control to obtain a p-score; determining the type of fibroepithelial tumour based on the p-score, wherein a p-score of less than 0.5 is indicative of fibroadenoma and a p-score of 0.5 and above is indicative of phyllodes tumour; and selecting the treatment of the patient based upon the type of fibroepithelial tumour and p-score.

It will be generally understood that the treatment of a subject with a fibroepithelial tumour of the breast may be tailored based on the indication of a malignant phyllodes tumour or a benign fibroadenoma.

In a third aspect, the present invention relates to a kit when used in the method of as described herein. The kit may comprise: a primer pair for amplifying the one or more genes selected from the group consisting of PRAME, ADH1B, CTHRC1, NPTX2, NEFL, ABCA8, DAPL1, TP63_v2, COL17A1, GCNT2, CCL19, MMP3, FN1, TRERF1, TRIM29, TESC, KIF20A, UHRF1, HEPACAM2, APOD, SERHL2, KIF15, HOXD13, GAGE2B, CALML5, C2orf40, ADH1C, CYP1B1, SPAG11B, GRB7, UBE2C, SYNGAP1, TP63_v1, LAMB1, OR5P3, SPC25, SHISA2, SCARA5, LHX2, RORC, DPYSL4, CH25H, and CHST1.

In one embodiment, the one or more genes may be selected from the group consisting of PRAME, TRIM29, FN1, CCL19, ABCA8, NPTX2 and APOD. In another embodiment, the one or more genes may consist of PRAME, FN1, CCL19, ABCA8, and APOD.

In one embodiment, the kit further comprises a primer pair for one or more normalized genes selected from the group consisting of RMRP, RPL18, RPLP2, SNORA61 and SNORA45. In a preferred embodiment, the one or more normalized genes may consist of RMRP, RPL18, RPLP2, SNORA61 and SNORA45.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1

Study Population

The study received approval from the Institutional Review Board. Forty eight formalin-fixed, paraffin embedded (FFPE) samples of fibroadenomas (FA) and phyllodes tumours (PT) were selected from the database of Department of Pathology, Singapore General Hospital (Table 1). Haematoxylin and eosin (H&E) stained slides were retrieved and reviewed. Diagnoses for the core biopsy samples were confirmed on corresponding excisions.

TABLE 1

Clinical features of the training cohort from 38 patients.

| Features | Fibro-adenomas (n = 19) | Phyllodes tumours (n = 19) | p-value |
|---|---|---|---|
| Age | | | |
| Median (range) | 35 (17-80) | 44 (18-64) | 0.09 |
| Size | | | |
| Median (range) | 25 (15-50) | 65 (25-220) | <0.001 |
| Ethnicity, n (%) | | | 0.2 |
| Chinese | 13 (68.4) | 11 (57.9) | |
| Malay | 0 (0.0) | 4 (21.0) | |
| Indian | 2 (10.5) | 1 (5.3) | |
| Others | 4 (21.1) | 3 (15.8) | |
| Histology | | | |
| Simple fibroadenoma | 15[a] | | |
| Complex fibroadenoma | 4[c] | | |
| Benign phyllodes tumour | | 13[b] | |

TABLE 1-continued

Clinical features of the training cohort from 38 patients.

| Features | Fibro-adenomas (n = 19) | Phyllodes tumours (n = 19) | p-value |
|---|---|---|---|
| Borderline phyllodes tumour | | 3[c] | |
| Malignant phyllodes tumour | | 3[c] | |

[a]5 paired core biopsies and surgical excisions;
[b]4 paired core biopsies and surgical excisions;
[c]1 paired core biopsy and surgical excision Example 2

Gene Expression Profiling

Sample Preparation and RNA Extraction

Representative tumour area was identified and marked. 3-7 sections of 10 μm sections from the same FFPE tumour block were obtained. Sections were deparaffinised in two changes of xylene for 2 minutes each then in three changes of absolute ethanol for 1 minute each. Macrodissection was performed immediately to retrieve the tumour area. RNA was extracted from the macrodissected tissue using the RNeasy FFPE kit (Qiagen, Germany) according to manufacturer's protocol with slight modifications. Briefly, buffer PKD and proteinase K was added after all ethanol was removed from the tissue. The tissue mixture was incubated overnight at 56° C. instead of 15 minutes as stated in the protocol, then it was incubated at 80° C. for 15 minutes followed by incubation on ice for 3 minutes. DNase I and DNase Booster Buffer was added and incubated in room temperature for 15 minutes after which buffer RBC was added to adjust for binding condition. Absolute ethanol was added and the entire lysate was then passed through a filter cartridge and washed with buffer RPE according to the manufacturer's instructions. Finally, RNA was eluted in 30 μl nuclease-free water and stored at −80° C. immediately.

Quality Assessment for RNA Extracted

RNA extracted was quantified by Nanodrop Spectrophotometer (Thermo Scientific, USA). 100 ng was used for quality assessment by real-time amplification of the RPL13A gene (forward primer, 5'-CACTTGGGGACAG-CATGAG-3' (SEQ ID NO: 1), and reverse primer, 5'-TAACCCCTTGGTTGTGCAT-3' (SEQ ID NO: 2) using the PowerSYBR® Green RNA-to-CT™ 1-Step Kit (Life Technologies, USA) on the CFX96™ Real-Time PCR machine (Bio-Rad Laboratories, USA), Samples with threshold cycle (Ct) below 29 passed for subsequent experiments.

Expression Profiling by Whole-Genome DASL HT Assay

1 μg of RNA were submitted for expression profiling at the Biopolis Shared Facilities, Agency of Science, Technology and Research (A*Star), Singapore. Samples were further subjected to quality assessment on a bioanalyzer before subjected to expression profiling on the Whole-Genome DASL (WG-DASL) HT Assay (Illumina, Inc., USA), The assay interrogates 29,377 features using the HumanHT-12 v4 BeadChip. Quantile-normalized gene expression data pre-analyzed using GenomeStudio® was delivered.

Selection of Normalization Genes

Normalization genes were selected based on the smallest value of coefficient of variance (mean/standard deviation) among all samples. Five genes with the least variable expression were selected. The genes are RMRP, RPL18, RPLP2, SNORA61, and SNORA45 (FIG. 1).

Selection of Potential Differentiating Genes

Significance Analysis of Microarrays (SAM, R version 3.1.1) was employed to select significant genes that were differentially expressed between phyllodes tumours (PT) and fibroadenomas (FA). Then, genes were filtered based on the following criteria: 1) q-value less than 0.05; 2) mean difference of expression above 500; 3) R-fold above 1.5 (for genes highly expressed in PT) or less than 0.67 (for genes highly expressed in FA). List of genes after criteria applied is shown in Table 2. 43 genes were selected from the list for downstream applications.

TABLE 2

Significant genes differentially expressed between fibroadenomas and *phyllodes* tumours.

| | Gene Name | Accession Number | Fold Change | q-value | Mean (FA) | Mean (PT) |
|---|---|---|---|---|---|---|
| 1 | CCL19* | NM_006274.2 | 0.238 | 0.000 | 6401.37 | 1462.00 |
| 2 | HEPACAM2* | NM_198151.1 | 0.297 | 0.000 | 3357.07 | 1204.56 |
| 3 | PRAME* | NM_206956.1 | 3.219 | 0.000 | 271.22 | 2356.54 |
| 4 | ADH1B* | NM_000668.3 | 0.317 | 0.000 | 1555.38 | 361.27 |
| 5 | LHX2* | NM_004789.3 | 3.017 | 0.000 | 192.15 | 873.55 |
| 6 | SCGB3A1 | NM_052863.2 | 0.342 | 0.000 | 4349.65 | 1425.53 |
| 7 | MAGEA4 | NM_002362.4 | 2.622 | 0.000 | 98.31 | 682.85 |
| 8 | C11orf87 | NM_207645.1 | 2.603 | 0.000 | 290.63 | 1187.03 |
| 9 | SCARA5* | NM_173833.3 | 0.384 | 0.000 | 5991.51 | 2661.17 |
| 10 | CALML5* | NM_017422.3 | 0.388 | 0.000 | 3366.04 | 1500.41 |
| 11 | ABCA8* | NM_007168.2 | 0.394 | 0.000 | 5788.98 | 2538.10 |
| 12 | C10orf65 | NM_138413.2 | 0.396 | 0.000 | 1356.30 | 476.13 |
| 13 | OR5P2 | NM_153444.1 | 0.401 | 0.000 | 2461.50 | 931.51 |
| 14 | HIST2H3C | NM_021059.2 | 2.492 | 0.000 | 410.84 | 1621.87 |
| 15 | ADAMTS14 | NM_139155.2 | 2.479 | 0.000 | 332.15 | 1041.68 |
| 16 | ADH1C* | NM_000669.3 | 0.414 | 0.000 | 1476.03 | 496.99 |
| 17 | DAPL1* | NM_001017920.1 | 0.415 | 0.000 | 1533.29 | 596.97 |
| 18 | CYP1B1* | NM_000104.2 | 0.416 | 0.000 | 3070.42 | 1223.42 |
| 19 | RORC* | NM_001001523.1 | 0.416 | 0.000 | 3369.06 | 1315.81 |
| 20 | INS-IGF2 | NM_001042377.1 | 2.395 | 0.000 | 1499.89 | 5149.56 |
| 21 | FBLN2 | NM_001004019.1 | 0.420 | 0.000 | 1819.30 | 621.23 |
| 22 | HMX1 | NM_018942.1 | 2.350 | 0.000 | 636.45 | 2066.76 |
| 23 | TOX3 | NM_001080430.1 | 0.429 | 0.000 | 1554.70 | 549.13 |
| 24 | UCN2 | NM_033199.3 | 2.315 | 0.000 | 201.58 | 808.36 |
| 25 | NPTX2* | NM_002523.1 | 2.307 | 0.000 | 534.04 | 2133.35 |

TABLE 2-continued

Significant genes differentially expressed between fibroadenomas and *phyllodes* tumours.

| | Gene Name | Accession Number | Fold Change | q-value | Mean (FA) | Mean (PT) |
|---|---|---|---|---|---|---|
| 26 | C1orf116 | NM_023938.4 | 0.450 | 0.000 | 6447.65 | 2744.49 |
| 27 | SLCO2A1 | NM_005630.1 | 0.451 | 0.000 | 2419.34 | 1179.40 |
| 28 | SPAG11B* | XM_943161.1 | 2.205 | 0.000 | 263.95 | 1319.11 |
| 29 | CHST1* | NM_003654.2 | 2.193 | 0.000 | 463.73 | 1758.28 |
| 30 | GATA4 | NM_002052.2 | 2.170 | 0.000 | 420.22 | 1044.98 |
| 31 | FOXL2 | NM_023067.2 | 2.163 | 0.000 | 298.64 | 851.84 |
| 32 | C11orf9 | NM_013279.1 | 2.153 | 0.000 | 2178.75 | 4718.14 |
| 33 | PTK6 | NM_005975.2 | 0.469 | 0.000 | 1625.63 | 594.36 |
| 34 | ALDH3A1 | NM_000691.3 | 0.476 | 0.000 | 1132.51 | 473.22 |
| 35 | SLC6A10P | NM_198857.1 | 2.098 | 0.000 | 836.63 | 2446.74 |
| 36 | DMD | NM_004006.1 | 0.477 | 0.000 | 4006.48 | 1884.54 |
| 37 | FOLR1 | NM_016724.1 | 0.480 | 0.000 | 3346.14 | 1464.66 |
| 38 | COL17A1* | NM_130778.1 | 0.480 | 0.000 | 5408.73 | 2820.70 |
| 39 | BMPER | NM_133468.3 | 2.078 | 0.000 | 442.89 | 1332.98 |
| 40 | TP63_v2* | NM_001114981.1 | 0.482 | 0.000 | 3334.76 | 1749.94 |
| 41 | OR5P3* | NM_153445.1 | 0.483 | 0.000 | 3498.35 | 1615.77 |
| 42 | CEP55 | NM_018131.3 | 2.068 | 0.000 | 620.51 | 1605.08 |
| 43 | UBE2C* | NM_181800.1 | 2.037 | 0.000 | 1083.86 | 3086.79 |
| 44 | RERGL | NM_024730.2 | 0.491 | 0.000 | 8754.38 | 4200.75 |
| 45 | CHRDL1 | NM_145234.2 | 0.493 | 0.000 | 964.70 | 434.81 |
| 46 | HIST2H3A | NM_001005464.2 | 2.023 | 0.000 | 1125.74 | 2996.04 |
| 47 | ARHGAP28 | NM_001010000.1 | 2.016 | 0.000 | 402.80 | 998.87 |
| 48 | RAB26 | NM_014353.4 | 0.499 | 0.000 | 2454.81 | 1086.37 |
| 49 | ITPKA | NM_002220.1 | 1.983 | 0.000 | 364.95 | 1256.14 |
| 50 | PIP5K1B | NM_003558.1 | 0.505 | 0.000 | 2060.46 | 874.85 |
| 51 | OVOL2 | NM_021220.2 | 0.508 | 0.000 | 3404.75 | 1731.30 |
| 52 | DPYSL4* | NM_006426.1 | 1.964 | 0.000 | 2600.24 | 6029.72 |
| 53 | GOLSYN | NM_017786.2 | 0.510 | 0.000 | 1196.96 | 649.42 |
| 54 | HAO2 | NM_016527.2 | 1.935 | 0.000 | 1094.93 | 2343.37 |
| 55 | ODF3B | NM_001014440.2 | 0.517 | 0.000 | 2348.32 | 975.50 |
| 56 | TRIO | NM_007118.2 | 1.931 | 0.000 | 983.89 | 2450.63 |
| 57 | OMD | NM_005014.1 | 0.518 | 0.000 | 2132.70 | 1094.13 |
| 58 | CCR6 | NM_031409.2 | 0.518 | 0.000 | 4754.45 | 1956.59 |
| 59 | TP63_v1* | NM_001114979.1 | 0.519 | 0.000 | 2294.56 | 1109.40 |
| 60 | SNORD114-11 | NR_003204.1 | 1.925 | 0.000 | 853.71 | 1982.01 |
| 61 | SCN2A | NM_021007.2 | 0.520 | 0.000 | 1381.68 | 678.87 |
| 62 | GNAO1 | NM_138736.1 | 0.522 | 0.000 | 2558.56 | 1387.49 |
| 63 | MYH11 | NM_001040114.1 | 0.524 | 0.000 | 10978.83 | 5947.62 |
| 64 | NUF2 | NM_031423.2 | 1.906 | 0.000 | 502.69 | 1134.83 |
| 65 | SORBS2 | NM_003603.4 | 0.525 | 0.000 | 2705.25 | 1260.39 |
| 66 | DMKN | NM_033317.2 | 0.530 | 0.000 | 5553.01 | 2875.06 |
| 67 | C2orf40* | NM_032411.1 | 0.533 | 0.000 | 7163.03 | 3881.54 |
| 68 | SNORD113-2 | NR_003230.1 | 1.860 | 0.000 | 2249.67 | 4955.17 |
| 69 | ICA1 | NM_004968.2 | 0.539 | 0.000 | 4094.35 | 2054.05 |
| 70 | TRPV6 | NM_018646.2 | 0.539 | 0.000 | 7207.76 | 3483.60 |
| 71 | CX3CR1 | NM_001337.3 | 0.543 | 0.000 | 2914.17 | 1294.22 |
| 72 | TRIM29* | NM_058193.1 | 0.550 | 0.000 | 2676.62 | 1509.53 |
| 73 | RORC* | NM_005060.3 | 0.550 | 0.000 | 1132.56 | 512.31 |
| 74 | BNC2 | NM_017637.4 | 1.814 | 0.000 | 672.28 | 1526.15 |
| 75 | CCL14 | NM_032962.2 | 0.553 | 0.000 | 5609.28 | 2625.91 |
| 76 | HIST1H2BO | NM_003527.4 | 1.807 | 0.000 | 903.41 | 2227.11 |
| 77 | BIK | NM_001197.3 | 0.553 | 0.000 | 4113.72 | 2168.46 |
| 78 | TPD52 | NM_005079.2 | 0.555 | 0.000 | 4477.83 | 2471.86 |
| 79 | ERBB3 | NM_001005915.1 | 0.557 | 0.000 | 2492.09 | 1233.05 |
| 80 | CPXM2 | NM_198148.1 | 0.558 | 0.000 | 1485.83 | 730.76 |
| 81 | KIF15* | NM_020242.1 | 1.771 | 0.000 | 845.62 | 1986.70 |
| 82 | C9orf61 | NM_004816.2 | 0.567 | 0.000 | 6350.94 | 3483.51 |
| 83 | CH25H* | NM_003956.2 | 1.758 | 0.000 | 3249.49 | 6596.97 |
| 84 | LOC387882 | NM_207376.1 | 1.733 | 0.000 | 2506.29 | 5511.78 |
| 85 | CDC2 | NM_033379.2 | 1.727 | 0.000 | 374.19 | 890.73 |
| 86 | SPRY4 | NM_030964.2 | 1.727 | 0.000 | 682.61 | 1601.01 |
| 87 | BCORL1 | NM_021946.2 | 1.711 | 0.000 | 578.68 | 1252.48 |
| 88 | VASH2 | NM_024749.2 | 1.695 | 0.000 | 868.19 | 1860.94 |
| 89 | APOD* | NM_001647.2 | 0.597 | 0.000 | 27261.88 | 14662.55 |
| 90 | SNORD114-2 | NR_003194.1 | 1.654 | 0.000 | 941.93 | 1938.27 |
| 91 | HIST1H2AB | NM_003513.2 | 1.649 | 0.000 | 998.86 | 2066.51 |
| 92 | IFIT2 | NM_001547.3 | 0.608 | 0.000 | 1615.48 | 834.68 |
| 93 | DPP4 | NM_001935.3 | 0.613 | 0.000 | 1642.02 | 867.59 |
| 94 | DMPK | NM_001081563.1 | 1.624 | 0.000 | 544.62 | 1072.50 |
| 95 | SV2A | NM_014849.2 | 1.624 | 0.000 | 3422.85 | 6383.33 |
| 96 | HOXA5 | NM_019102.2 | 0.629 | 0.000 | 9540.64 | 5156.14 |
| 97 | NTRK2 | NM_001018065.1 | 0.633 | 0.000 | 14191.59 | 8187.81 |
| 98 | LOC653604 | NM_001025303.1 | 1.568 | 0.000 | 2227.40 | 4100.91 |

TABLE 2-continued

Significant genes differentially expressed between fibroadenomas and *phyllodes* tumours.

| | Gene Name | Accession Number | Fold Change | q-value | Mean (FA) | Mean (PT) |
|---|---|---|---|---|---|---|
| 99 | UCHL1 | NM_004181.3 | 1.562 | 0.000 | 6265.88 | 11750.85 |
| 100 | ARSB | NM_000046.2 | 1.561 | 0.000 | 738.12 | 1382.59 |
| 101 | LAMB1 | NM_002291.1 | 1.555 | 0.000 | 2604.77 | 4853.49 |
| 102 | CD79A | NM_001783.2 | 0.645 | 0.000 | 11756.75 | 6159.25 |
| 103 | FN1* | NM_212474.1 | 1.543 | 0.000 | 10854.37 | 19701.55 |
| 104 | MAGED4 | NM_001098800.1 | 1.535 | 0.000 | 3817.08 | 6777.09 |
| 105 | COL5A2 | NM_000393.2 | 1.528 | 0.000 | 5377.06 | 9945.28 |
| 106 | CTAG1B | NM_001327.1 | 3.267 | 0.005 | 351.12 | 2708.49 |
| 107 | HOXD13* | NM_000523.2 | 2.923 | 0.005 | 1228.70 | 2928.62 |
| 108 | PRAME* | NM_206955.1 | 2.720 | 0.005 | 315.35 | 1564.15 |
| 109 | CYTL1 | NM_018659.2 | 2.451 | 0.005 | 215.23 | 1102.61 |
| 110 | HMGA2 | NM_001015886.1 | 2.388 | 0.005 | 338.52 | 1072.97 |
| 111 | KRT3 | NM_057088.1 | 2.242 | 0.005 | 477.76 | 1757.73 |
| 112 | KIF20A* | NM_005733.1 | 2.200 | 0.005 | 621.79 | 1867.56 |
| 113 | CKAP2L | NM_152515.2 | 2.153 | 0.005 | 1131.57 | 2246.70 |
| 114 | CHD5 | NM_015557.1 | 2.134 | 0.005 | 617.17 | 2465.83 |
| 115 | ASPHD1 | NM_181718.3 | 2.052 | 0.005 | 653.11 | 1578.02 |
| 116 | CDC42 | NM_044472.1 | 2.037 | 0.005 | 611.55 | 1347.53 |
| 117 | WISP1 | NM_003882.2 | 1.971 | 0.005 | 323.17 | 1120.21 |
| 118 | TGFB2 | NM_003238.1 | 1.965 | 0.005 | 1485.78 | 3583.24 |
| 119 | C6orf134 | NM_024909.1 | 1.830 | 0.005 | 1976.87 | 3958.66 |
| 120 | NECAB2 | NM_019065.2 | 1.826 | 0.005 | 320.83 | 861.02 |
| 121 | HSP90B3P | NR_003130.1 | 1.785 | 0.005 | 2346.80 | 4540.93 |
| 122 | MCM4 | NM_182746.1 | 1.776 | 0.005 | 740.07 | 1454.59 |
| 123 | FAM72D | NM_207418.2 | 1.774 | 0.005 | 672.94 | 1521.88 |
| 124 | GLIS1 | NM_147193.1 | 1.773 | 0.005 | 1621.56 | 3544.42 |
| 125 | ARHGAP28 | NM_030672.2 | 1.723 | 0.005 | 405.31 | 925.08 |
| 126 | HCFC1R1 | NM_001002018.1 | 1.682 | 0.005 | 1110.66 | 2362.14 |
| 127 | MEX3A | NM_001093725.1 | 1.682 | 0.005 | 502.95 | 1145.83 |
| 128 | UHRF1* | NM_013282.2 | 1.679 | 0.005 | 1364.77 | 2768.18 |
| 129 | SRPX2 | NM_014467.1 | 1.511 | 0.005 | 3786.75 | 6682.12 |
| 130 | TNFRSF19 | NM_148957.2 | 1.505 | 0.005 | 3534.15 | 6462.72 |
| 131 | OLFM4 | NM_006418.3 | 0.425 | 0.006 | 4922.09 | 1865.57 |
| 132 | MYBPC1 | NM_002465.2 | 0.442 | 0.006 | 8807.86 | 4325.10 |
| 133 | MBP | NM_001025100.1 | 0.450 | 0.006 | 2337.70 | 1170.46 |
| 134 | ITGB4 | NM_001005731.1 | 0.496 | 0.006 | 8161.34 | 4380.08 |
| 135 | SEMA3C | NM_006379.2 | 0.499 | 0.006 | 1738.78 | 939.67 |
| 136 | TNXA | NR_001284.1 | 0.503 | 0.006 | 2870.44 | 1536.83 |
| 137 | ABCA6 | NM_172346.1 | 0.507 | 0.006 | 2887.42 | 1689.39 |
| 138 | CDH3 | NM_001793.3 | 0.509 | 0.006 | 1727.21 | 797.36 |
| 139 | MMP3* | NM_002422.3 | 0.509 | 0.006 | 7370.34 | 3440.73 |
| 140 | IGJ | NM_144646.2 | 0.525 | 0.006 | 11657.95 | 5536.68 |
| 141 | MPPED2 | NM_001584.1 | 0.530 | 0.006 | 1800.18 | 855.69 |
| 142 | ESRP2 | NM_024939.2 | 0.532 | 0.006 | 1396.29 | 806.60 |
| 143 | KIAA1543 | NM_001080429.1 | 0.533 | 0.006 | 7813.91 | 4351.06 |
| 144 | LRRC26 | XM_939320.1 | 0.534 | 0.006 | 21534.63 | 11639.52 |
| 145 | CISH | NM_145071.1 | 0.547 | 0.006 | 1111.81 | 503.47 |
| 146 | CD300LG | NM_145273.2 | 0.550 | 0.006 | 6029.22 | 3428.30 |
| 147 | NAAA | NM_014435.2 | 0.554 | 0.006 | 2540.54 | 1383.43 |
| 148 | NTF5 | NM_006179.3 | 0.559 | 0.006 | 1552.44 | 873.81 |
| 149 | GCNT2* | NM_001491.2 | 0.565 | 0.006 | 1244.85 | 591.56 |
| 150 | BEND7 | NM_152751.2 | 0.579 | 0.006 | 2081.16 | 1150.16 |
| 151 | ADHFE1 | NM_001077593.1 | 0.581 | 0.006 | 2700.68 | 1486.68 |
| 152 | TMTC1 | XM_928461.1 | 0.599 | 0.006 | 1775.89 | 950.71 |
| 153 | ZNF683 | NM_173574.1 | 0.602 | 0.006 | 1186.86 | 588.88 |
| 154 | LAMA3 | NM_000227.2 | 0.603 | 0.006 | 3102.16 | 1699.84 |
| 155 | SLC44A4 | NM_025257.1 | 0.607 | 0.006 | 1634.05 | 775.09 |
| 156 | SPNS2 | NM_001124758.1 | 0.608 | 0.006 | 2337.54 | 1176.42 |
| 157 | C3 | XM_941913.1 | 0.613 | 0.006 | 3019.27 | 1790.95 |
| 158 | PKIB | NM_032471.4 | 0.615 | 0.006 | 9669.95 | 5673.26 |
| 159 | RNF39 | NM_025236.2 | 0.617 | 0.006 | 6629.28 | 3876.69 |
| 160 | ZMAT1 | NM_032441.1 | 0.628 | 0.006 | 4823.99 | 2857.70 |
| 161 | COL8A2 | NM_005202.1 | 0.656 | 0.006 | 1654.50 | 999.00 |
| 162 | FAM113B | NM_138371.1 | 0.664 | 0.006 | 11107.68 | 6668.04 |
| 163 | CTHRC1* | NM_138455.2 | 1.629 | 0.008 | 1404.03 | 4266.54 |
| 164 | HOXC10 | NM_017409.2 | 1.519 | 0.008 | 1145.45 | 1960.25 |
| 165 | SERHL2* | NM_014509.3 | 0.469 | 0.009 | 3005.44 | 1304.93 |
| 166 | IL17RE | NM_153480.1 | 0.481 | 0.009 | 1020.90 | 451.33 |
| 167 | FAM46C | NM_017709.2 | 0.566 | 0.009 | 3404.03 | 1754.54 |
| 168 | NTF4 | NM_006179.4 | 0.591 | 0.009 | 1681.80 | 822.32 |
| 169 | PDZD2 | NM_178140.1 | 0.599 | 0.009 | 1892.49 | 1080.48 |
| 170 | DST | NM_183380.1 | 0.625 | 0.009 | 6094.06 | 3547.30 |
| 171 | FAM13AOS | NR_002806.2 | 0.640 | 0.009 | 1792.17 | 1060.99 |
| 172 | NEFL* | NM_006158.1 | 2.235 | 0.011 | 1207.97 | 3800.96 |

TABLE 2-continued

Significant genes differentially expressed between fibroadenomas and *phyllodes* tumours.

| | Gene Name | Accession Number | Fold Change | q-value | Mean (FA) | Mean (PT) |
|---|---|---|---|---|---|---|
| 173 | ADAMTS14 | NM_139155.1 | 2.147 | 0.011 | 741.49 | 2476.27 |
| 174 | GAGE8 | NM_012196.1 | 2.136 | 0.011 | 76.18 | 606.27 |
| 175 | SEMA7A | NM_003612.1 | 1.679 | 0.011 | 466.84 | 1225.51 |
| 176 | ADAMTS4 | NM_005099.3 | 1.643 | 0.011 | 415.61 | 1061.23 |
| 177 | IGDCC4 | NM_020962.1 | 1.615 | 0.011 | 1416.17 | 2674.22 |
| 178 | ZNF697 | NM_001080470.1 | 1.586 | 0.011 | 1769.98 | 3270.23 |
| 179 | KIF23 | NM_138555.1 | 1.562 | 0.011 | 1592.93 | 2855.64 |
| 180 | LMNA | NM_005572.2 | 1.556 | 0.011 | 1366.60 | 2708.40 |
| 181 | TMEM167A | NM_174909.1 | 1.543 | 0.011 | 1034.23 | 2030.24 |
| 182 | GPR144 | NM_182611.1 | 0.399 | 0.012 | 2233.07 | 1377.46 |
| 183 | ANXA8L1 | NM_001098845.1 | 0.443 | 0.012 | 2553.16 | 1366.48 |
| 184 | FGF12 | NM_004113.3 | 0.481 | 0.012 | 3232.40 | 1532.51 |
| 185 | PRR22 | NM_153359.1 | 0.505 | 0.012 | 1131.53 | 520.07 |
| 186 | B3GALT1 | NM_020981.2 | 0.518 | 0.012 | 1950.99 | 987.39 |
| 187 | SNCG | NM_003087.1 | 0.521 | 0.012 | 2253.34 | 1014.55 |
| 188 | TJP2 | NM_201629.1 | 0.526 | 0.012 | 1240.59 | 691.40 |
| 189 | NSUN7 | NM_024677.3 | 0.528 | 0.012 | 1867.16 | 901.46 |
| 190 | CRB3 | NM_139161.2 | 0.542 | 0.012 | 1254.51 | 648.64 |
| 191 | GCNT2* | NM_145649.2 | 0.550 | 0.012 | 1919.87 | 908.79 |
| 192 | SHROOM3 | NM_020859.3 | 0.551 | 0.012 | 1795.73 | 922.72 |
| 193 | MAL | NM_022440.1 | 0.565 | 0.012 | 949.74 | 390.12 |
| 194 | DYNLRB2 | NM_130897.1 | 0.569 | 0.012 | 4168.95 | 2474.99 |
| 195 | MATN2 | NM_030583.2 | 0.574 | 0.012 | 10052.44 | 6120.20 |
| 196 | SOX10 | NM_006941.3 | 0.584 | 0.012 | 9462.89 | 5634.60 |
| 197 | PSD4 | NM_012455.2 | 0.586 | 0.012 | 8086.61 | 4639.92 |
| 198 | ELANE | NM_001972.2 | 0.592 | 0.012 | 1889.14 | 1072.16 |
| 199 | RASSF6 | NM_177532.3 | 0.601 | 0.012 | 4752.93 | 2773.06 |
| 200 | IRX1 | NM_024337.3 | 0.602 | 0.012 | 2571.54 | 1439.00 |
| 201 | C5orf4 | NM_016348.1 | 0.617 | 0.012 | 3890.59 | 2308.86 |
| 202 | NTRK2 | NM_001007097.1 | 0.619 | 0.012 | 11514.66 | 6827.91 |
| 203 | NDRG2 | NM_201539.1 | 0.630 | 0.012 | 5569.99 | 3347.51 |
| 204 | SMOC2 | NM_022138.1 | 0.643 | 0.012 | 4976.71 | 3154.28 |
| 205 | PGM5 | NM_021965.3 | 0.644 | 0.012 | 1755.43 | 1094.11 |
| 206 | PDGFD | NM_025208.3 | 0.655 | 0.012 | 3886.45 | 2311.57 |
| 207 | N4BP2L1 | NM_001079691.1 | 0.660 | 0.012 | 6019.26 | 3611.31 |
| 208 | EPHA1 | NM_005232.3 | 0.661 | 0.012 | 3800.40 | 2364.55 |
| 209 | PAGE2B | NM_001015038.1 | 2.368 | 0.013 | 673.59 | 2715.27 |
| 210 | SULT2B1 | NM_177973.1 | 0.489 | 0.013 | 1740.07 | 753.08 |
| 211 | DUSP4 | NM_001394.5 | 0.503 | 0.013 | 1331.30 | 773.25 |
| 212 | FRMPD2 | NM_001018071.2 | 0.518 | 0.013 | 1236.62 | 522.52 |
| 213 | TSPAN7 | NM_004615.2 | 0.541 | 0.013 | 2888.02 | 1471.26 |
| 214 | C9orf47 | NM_001001938.1 | 1.819 | 0.013 | 548.08 | 1312.29 |
| 215 | C6orf134 | NM_001031722.1 | 1.723 | 0.013 | 897.08 | 1932.25 |
| 216 | COL12A1 | NM_080645.1 | 1.722 | 0.013 | 539.58 | 1451.54 |
| 217 | NR1D1 | NM_021724.1 | 1.707 | 0.013 | 2301.41 | 4716.38 |
| 218 | SHANK2 | NM_012309.1 | 0.588 | 0.013 | 5854.52 | 3360.51 |
| 219 | ABCA6 | NM_080284.2 | 0.608 | 0.013 | 3315.73 | 1790.29 |
| 220 | LRRC20 | NM_018239.2 | 1.640 | 0.013 | 824.08 | 1772.58 |
| 221 | REEP4 | NM_025232.2 | 1.616 | 0.013 | 2039.11 | 3741.07 |
| 222 | ERBB3 | NM_001982.2 | 0.619 | 0.013 | 3119.59 | 1943.86 |
| 223 | FMO2 | NM_001460.2 | 0.620 | 0.013 | 12042.98 | 6604.46 |
| 224 | SYNE2 | NM_015180.3 | 0.622 | 0.013 | 2511.72 | 1472.52 |
| 225 | CDCA4 | NM_017955.2 | 1.592 | 0.013 | 3161.08 | 5549.14 |
| 226 | CYYR1 | NM_052954.2 | 0.644 | 0.013 | 1844.54 | 1083.32 |
| 227 | SYNGAP1* | NM_006772.1 | 1.913 | 0.014 | 2589.28 | 4932.32 |
| 228 | EMILIN1 | NM_007046.1 | 1.776 | 0.014 | 3037.94 | 7187.87 |
| 229 | STMN1 | NM_005563.3 | 1.743 | 0.014 | 451.33 | 961.24 |
| 230 | FAM38B | NM_022068.1 | 1.725 | 0.014 | 778.49 | 1721.00 |
| 231 | RAB23 | NM_016277.3 | 1.635 | 0.014 | 1576.94 | 3283.62 |
| 232 | HOXA11AS | NR_002795.2 | 1.634 | 0.014 | 934.89 | 1954.07 |
| 233 | TRERF1* | XM_945260.1 | 1.512 | 0.014 | 800.39 | 1212.20 |
| 234 | PI16 | NM_153370.2 | 0.448 | 0.015 | 12074.86 | 6681.91 |
| 235 | HGD | NM_000187.2 | 0.515 | 0.015 | 2866.55 | 1752.37 |
| 236 | ANXA8L2 | NM_001630.2 | 0.517 | 0.015 | 2506.01 | 1527.62 |
| 237 | MAPT | NM_016841.2 | 0.517 | 0.015 | 1483.95 | 822.41 |
| 238 | C11orf92 | NM_207429.2 | 0.523 | 0.015 | 1791.35 | 897.45 |
| 239 | MIR200A | NR_029834.1 | 0.536 | 0.015 | 1228.69 | 515.17 |
| 240 | TNFRSF13B | NM_012452.2 | 0.568 | 0.015 | 2609.63 | 1538.91 |
| 241 | WISP3 | NM_003880.2 | 0.570 | 0.015 | 2394.62 | 1393.60 |
| 242 | STX19 | NM_001001850.1 | 0.573 | 0.015 | 5365.54 | 2974.33 |
| 243 | STRC | NM_153700.2 | 0.589 | 0.015 | 1667.49 | 859.88 |
| 244 | IL20RA | NM_014432.2 | 0.599 | 0.015 | 1343.94 | 768.76 |
| 245 | GGT6 | NM_153338.1 | 0.600 | 0.015 | 2952.64 | 1700.81 |
| 246 | WDR17 | NM_170710.3 | 0.617 | 0.015 | 1416.91 | 866.17 |

TABLE 2-continued

Significant genes differentially expressed between fibroadenomas and *phyllodes* tumours.

| | Gene Name | Accession Number | Fold Change | q-value | Mean (FA) | Mean (PT) |
|---|---|---|---|---|---|---|
| 247 | TSTD1 | NM_001113206.1 | 0.619 | 0.015 | 2282.38 | 1378.68 |
| 248 | DSC3 | NM_024423.1 | 0.652 | 0.015 | 5069.04 | 3017.29 |
| 249 | MBP | NM_001025101.1 | 0.654 | 0.015 | 1236.99 | 667.97 |
| 250 | NET1 | NM_005863.2 | 0.661 | 0.015 | 3705.97 | 2330.58 |
| 251 | FAM129A | NM_022083.1 | 0.664 | 0.015 | 6734.51 | 4255.89 |
| 252 | N4BP2L1 | NM_052818.1 | 0.667 | 0.015 | 6217.91 | 3817.98 |
| 253 | PIP | NM_002652.2 | 0.397 | 0.016 | 6718.19 | 2296.33 |
| 254 | TP73L | NM_003722.3 | 0.430 | 0.016 | 2113.29 | 1084.30 |
| 255 | SCGB1D2 | NM_006551.3 | 0.460 | 0.016 | 4848.27 | 1515.54 |
| 256 | SHISA2* | NM_001007538.1 | 1.949 | 0.016 | 958.25 | 2011.20 |
| 257 | PCSK1 | NM_000439.3 | 1.914 | 0.016 | 98.86 | 719.27 |
| 258 | FXYD3 | NM_021910.1 | 0.537 | 0.016 | 2357.88 | 1411.76 |
| 259 | MARVELD3 | NM_052858.3 | 0.572 | 0.016 | 1979.64 | 1247.22 |
| 260 | EFEMP1 | NM_004105.2 | 0.600 | 0.016 | 3088.12 | 1602.20 |
| 261 | KIF11 | NM_004523.2 | 1.658 | 0.016 | 681.89 | 1574.32 |
| 262 | HIST1H2AJ | NM_021066.2 | 1.650 | 0.016 | 1430.62 | 3077.09 |
| 263 | PDGFD | NM_025208.4 | 0.614 | 0.016 | 3768.43 | 1961.56 |
| 264 | SLC44A4 | NM_032794.1 | 0.631 | 0.016 | 1673.40 | 813.44 |
| 265 | MFSD6 | NM_017694.2 | 0.638 | 0.016 | 2501.20 | 1604.12 |
| 266 | SLC29A4 | NM_001040661.1 | 1.505 | 0.016 | 3231.92 | 5597.04 |
| 267 | CASC5 | NM_170589.2 | 1.914 | 0.017 | 651.06 | 1422.31 |
| 268 | CENPE | NM_001813.2 | 1.634 | 0.017 | 500.28 | 1002.10 |
| 269 | KDM6B | NM_001080424.1 | 1.622 | 0.017 | 1544.49 | 2639.29 |
| 270 | BCAT1 | NM_005504.4 | 1.596 | 0.017 | 1515.63 | 3364.82 |
| 271 | PGAM4 | NM_001029891.2 | 1.592 | 0.017 | 2255.10 | 4830.64 |
| 272 | PCDH19 | NM_020766.1 | 1.525 | 0.017 | 1203.45 | 2194.59 |
| 273 | TFCP2L1 | NM_014553.1 | 0.498 | 0.018 | 2441.00 | 1391.77 |
| 274 | CMTM8 | NM_178868.3 | 0.507 | 0.018 | 10265.71 | 6375.56 |
| 275 | EDN3 | NM_207033.1 | 0.523 | 0.018 | 5356.67 | 3193.40 |
| 276 | SULT1A1 | NM_177536.1 | 0.543 | 0.018 | 1935.16 | 1032.19 |
| 277 | ABCA5 | NM_018672.2 | 0.570 | 0.018 | 2016.20 | 1106.86 |
| 278 | EPS8L2 | NM_022772.2 | 0.571 | 0.018 | 2217.34 | 1283.15 |
| 279 | TMTC1 | NM_175861.1 | 0.582 | 0.018 | 2098.08 | 1387.73 |
| 280 | ROPN1B | NM_001012337.1 | 0.594 | 0.018 | 1135.64 | 607.63 |
| 281 | ZBTB16 | NM_006006.4 | 0.599 | 0.018 | 4783.21 | 2884.79 |
| 282 | FLJ25996 | NM_001001699.1 | 0.605 | 0.018 | 5190.08 | 3538.10 |
| 283 | CYB5R2 | NM_016229.2 | 0.607 | 0.018 | 1958.89 | 1175.93 |
| 284 | WNT5B | NM_030775.2 | 0.614 | 0.018 | 2648.34 | 1652.66 |
| 285 | KLC3 | NM_145275.1 | 0.647 | 0.018 | 1280.21 | 696.36 |
| 286 | CYP2J2 | NM_000775.2 | 0.661 | 0.018 | 5849.76 | 3598.37 |
| 287 | GAGE2B* | NM_001098411.3 | 2.931 | 0.019 | 1195.21 | 4768.49 |
| 288 | SNORD113-8 | NR_003236.1 | 1.886 | 0.019 | 1751.83 | 3389.32 |
| 289 | CAMK2B | XM_936314.1 | 0.536 | 0.019 | 1407.32 | 596.51 |
| 290 | ZBTB16 | NM_001018011.1 | 0.542 | 0.019 | 5137.94 | 2829.86 |
| 291 | ATP13A4 | NM_032279.2 | 0.548 | 0.019 | 1933.93 | 1059.11 |
| 292 | ITIH5 | NM_030569.3 | 0.550 | 0.019 | 5602.73 | 3009.71 |
| 293 | C9orf152 | NM_001012993.1 | 0.555 | 0.019 | 6449.96 | 3891.87 |
| 294 | TSPAN18 | NM_130783.2 | 1.803 | 0.019 | 932.19 | 1966.51 |
| 295 | ASPM | NM_018136.2 | 1.737 | 0.019 | 352.06 | 887.25 |
| 296 | MUC16 | NM_024690.2 | 0.597 | 0.019 | 2027.26 | 969.68 |
| 297 | SEMA6B | NM_020241.2 | 1.631 | 0.019 | 536.99 | 1059.44 |
| 298 | NID2 | NM_007361.2 | 1.577 | 0.019 | 1365.27 | 2905.18 |
| 299 | HLA-DOA | NM_002119.3 | 0.655 | 0.019 | 3773.82 | 2448.04 |
| 300 | SAMD3 | NM_001017373.2 | 0.509 | 0.021 | 1781.17 | 1014.57 |
| 301 | BARX2 | NM_003658.3 | 0.557 | 0.021 | 3897.03 | 2346.09 |
| 302 | MAMDC2 | NM_153267.3 | 0.583 | 0.021 | 2044.78 | 1282.76 |
| 303 | LYPLAL1 | NM_138794.1 | 0.591 | 0.021 | 3499.07 | 2176.27 |
| 304 | TTC22 | NM_017904.1 | 0.593 | 0.021 | 2382.69 | 1426.62 |
| 305 | HJURP | NM_018410.2 | 1.679 | 0.021 | 576.16 | 1302.81 |
| 306 | MIR770 | NR_030528.1 | 1.664 | 0.021 | 482.61 | 1022.51 |
| 307 | ARHGAP8 | NM_001017526.1 | 0.601 | 0.021 | 3786.67 | 2482.97 |
| 308 | SNORD114-4 | NR_003196.1 | 1.655 | 0.021 | 2341.72 | 4519.16 |
| 309 | DBI | NM_020548.4 | 0.610 | 0.021 | 1515.89 | 789.03 |
| 310 | LMX1B | NM_002316.1 | 0.618 | 0.021 | 6460.47 | 4118.79 |
| 311 | CCNDBP1 | NM_037370.1 | 0.628 | 0.021 | 4950.25 | 3139.22 |
| 312 | SPDEF | NM_012391.1 | 0.632 | 0.021 | 6304.32 | 4204.84 |
| 313 | ACSM3 | NM_005622.3 | 0.638 | 0.021 | 1450.26 | 842.78 |
| 314 | FZD8 | NM_031866.1 | 0.645 | 0.021 | 4235.97 | 2336.29 |
| 315 | B4GALNT4 | NM_178537.3 | 1.514 | 0.021 | 1775.68 | 3431.11 |
| 316 | KIT | NM_000222.1 | 0.665 | 0.021 | 5842.05 | 3569.12 |
| 317 | EFEMP1 | NM_001039348.1 | 0.666 | 0.021 | 9176.93 | 5680.13 |
| 318 | PIGR | NM_002644.2 | 0.473 | 0.024 | 5371.20 | 3060.51 |
| 319 | PKIA | NM_006823.2 | 0.526 | 0.024 | 2815.33 | 1840.94 |
| 320 | CASC5 | NM_144508.2 | 1.783 | 0.024 | 495.59 | 1209.52 |

TABLE 2-continued

Significant genes differentially expressed between fibroadenomas and *phyllodes* tumours.

| | Gene Name | Accession Number | Fold Change | q-value | Mean (FA) | Mean (PT) |
|---|---|---|---|---|---|---|
| 321 | ITGA10 | NM_003637.3 | 0.569 | 0.024 | 5208.86 | 3166.58 |
| 322 | KRT8 | NM_002273.2 | 0.572 | 0.024 | 4770.01 | 3155.17 |
| 323 | EHF | NM_012153.3 | 0.581 | 0.024 | 2114.14 | 1148.85 |
| 324 | CDCA5 | NM_080668.2 | 1.713 | 0.024 | 739.56 | 1717.33 |
| 325 | MTL5 | NM_001039656.1 | 0.591 | 0.024 | 2604.36 | 1552.11 |
| 326 | SPC25* | NM_020675.3 | 1.650 | 0.024 | 3789.65 | 6657.18 |
| 327 | RNASE4 | NM_194431.1 | 0.611 | 0.024 | 1166.43 | 658.99 |
| 328 | RNF157 | NM_052916.1 | 1.633 | 0.024 | 477.55 | 1091.62 |
| 329 | COX6B2 | NM_144613.4 | 0.616 | 0.024 | 3268.01 | 1867.65 |
| 330 | FAM3B | NM_206964.1 | 0.618 | 0.024 | 1426.27 | 789.44 |
| 331 | MGC29506 | NM_016459.3 | 0.620 | 0.024 | 2898.60 | 1629.18 |
| 332 | LRRC50 | NM_178452.3 | 0.624 | 0.024 | 1152.82 | 627.97 |
| 333 | BNIPL | NM_138278.1 | 0.624 | 0.024 | 4963.78 | 2946.57 |
| 334 | NTRK2 | NM_006180.3 | 0.633 | 0.024 | 2816.20 | 1784.07 |
| 335 | LAMA2 | NM_000426.3 | 1.565 | 0.024 | 677.43 | 1352.44 |
| 336 | SERINC2 | NM_178865.3 | 0.648 | 0.024 | 8187.12 | 5309.52 |
| 337 | EFNA5 | NM_001962.1 | 0.655 | 0.024 | 4359.47 | 2731.05 |
| 338 | COL6A2 | NM_058175.1 | 1.523 | 0.024 | 1450.53 | 2881.49 |
| 339 | MYO5C | NM_018728.1 | 0.660 | 0.024 | 8300.77 | 5500.42 |
| 340 | THRSP | NM_003251.2 | 0.531 | 0.026 | 4300.49 | 2469.22 |
| 341 | DLGAP5 | NM_014750.3 | 1.879 | 0.026 | 1789.26 | 4417.65 |
| 342 | ASTN1 | NM_207108.1 | 1.846 | 0.026 | 467.61 | 1188.01 |
| 343 | KIAA1984 | NM_032874.2 | 0.548 | 0.026 | 7246.09 | 4458.80 |
| 344 | JSRP1 | NM_144616.2 | 0.575 | 0.026 | 5256.86 | 3081.64 |
| 345 | EMID2 | NM_133457.2 | 1.734 | 0.026 | 645.89 | 1485.35 |
| 346 | MEFV | NM_000243.1 | 0.613 | 0.026 | 1857.90 | 1180.01 |
| 347 | PKP2 | NM_001005242.1 | 0.614 | 0.026 | 2878.62 | 1781.03 |
| 348 | TMEM2 | NM_013390.1 | 1.617 | 0.026 | 1111.91 | 1990.57 |
| 349 | SLC44A3 | NM_152369.2 | 0.631 | 0.026 | 3943.79 | 2664.42 |
| 350 | C4orf42 | NM_052861.2 | 1.561 | 0.026 | 537.87 | 1416.00 |
| 351 | ICA1 | NM_022308.1 | 0.651 | 0.026 | 5503.17 | 3489.97 |
| 352 | SERPINB5 | NM_002639.2 | 0.654 | 0.026 | 3795.07 | 2489.94 |
| 353 | VIPR1 | NM_004624.2 | 0.663 | 0.026 | 44907.00 | 28943.51 |
| 354 | DNMT3A | NM_153759.2 | 1.500 | 0.026 | 642.00 | 1219.48 |
| 355 | CYP4F22 | NM_173483.1 | 0.538 | 0.027 | 4583.85 | 3015.48 |
| 356 | IFI44L | NM_006820.1 | 0.556 | 0.027 | 6717.39 | 3944.43 |
| 357 | LY6H | NM_002347.2 | 1.748 | 0.027 | 1181.70 | 3958.99 |
| 358 | PTPRT | NM_007050.4 | 0.581 | 0.027 | 2900.76 | 1835.73 |
| 359 | C5orf30 | NM_033211.2 | 0.586 | 0.027 | 6103.19 | 3928.24 |
| 360 | FAM46B | NM_052943.2 | 0.618 | 0.027 | 1406.61 | 766.40 |
| 361 | EPCAM | NM_002354.2 | 0.640 | 0.027 | 3360.87 | 2159.08 |
| 362 | AKAP1 | NM_003488.2 | 0.657 | 0.027 | 2219.99 | 1265.73 |
| 363 | TCEAL2 | NM_080390.3 | 0.462 | 0.030 | 2006.16 | 644.54 |
| 364 | CLDN7 | NM_001307.3 | 0.471 | 0.030 | 1188.53 | 451.41 |
| 365 | HLA-DQB2 | NM_182549.1 | 0.510 | 0.030 | 1731.84 | 508.03 |
| 366 | PIK3C2G | NM_004570.2 | 0.532 | 0.030 | 2463.15 | 1209.12 |
| 367 | MAOA | NM_000240.2 | 0.538 | 0.030 | 7781.94 | 3947.87 |
| 368 | CEACAM1 | NM_001024912.1 | 0.545 | 0.030 | 9683.05 | 5880.59 |
| 369 | PPP1R1A | NM_006741.2 | 0.547 | 0.030 | 949.35 | 413.73 |
| 370 | MAGEA9B | NM_001080790.1 | 1.806 | 0.030 | 199.68 | 726.71 |
| 371 | GRB7* | NM_005310.2 | 0.561 | 0.030 | 2054.91 | 1095.71 |
| 372 | FOXJ1 | NM_001454.2 | 1.754 | 0.030 | 229.46 | 780.35 |
| 373 | NETO1 | NM_138966.2 | 1.700 | 0.030 | 1067.26 | 1959.71 |
| 374 | TESC* | NM_017899.1 | 0.598 | 0.030 | 2449.50 | 1573.30 |
| 375 | NRG1 | NM_013961.1 | 0.599 | 0.030 | 2300.46 | 1365.91 |
| 376 | MGST1 | NM_020300.3 | 0.608 | 0.030 | 3726.89 | 2315.80 |
| 377 | LAMB3 | NM_000228.2 | 0.610 | 0.030 | 6255.97 | 3475.73 |
| 378 | MANEAL | NM_001031740.1 | 0.613 | 0.030 | 3173.76 | 1923.89 |
| 379 | CASZ1 | NM_017766.2 | 0.622 | 0.030 | 6722.05 | 4295.98 |
| 380 | FSD1 | NM_024333.1 | 1.580 | 0.030 | 678.13 | 1489.33 |
| 381 | HLF | NM_002126.3 | 0.639 | 0.030 | 5116.98 | 3500.22 |
| 382 | MNDA | NM_002432.1 | 0.639 | 0.030 | 2792.82 | 1720.02 |
| 383 | PTTG1 | NM_004219.2 | 1.563 | 0.030 | 1212.25 | 2590.68 |
| 384 | MFI2 | NM_005929.3 | 0.653 | 0.030 | 2075.84 | 1210.85 |
| 385 | FAM180A | NM_205855.2 | 0.658 | 0.030 | 2096.69 | 1318.29 |
| 386 | RASSF5 | NM_182664.1 | 0.664 | 0.030 | 1721.08 | 1041.90 |
| 387 | VAV3 | NM_006113.4 | 0.402 | 0.033 | 8116.96 | 5195.56 |
| 388 | ZNF365 | NM_199451.1 | 2.203 | 0.033 | 1153.31 | 2682.04 |
| 389 | SCRG1 | NM_007281.1 | 0.506 | 0.033 | 1859.99 | 735.93 |
| 390 | SLC15A3 | NM_016582.1 | 0.534 | 0.033 | 3705.00 | 2429.71 |
| 391 | SNORD113-3 | NR_003231.1 | 1.834 | 0.033 | 1276.34 | 2584.28 |
| 392 | RASL10B | NM_033315.2 | 1.788 | 0.033 | 791.38 | 1563.66 |
| 393 | TRIM36 | NM_001017397.1 | 0.560 | 0.033 | 2257.09 | 1326.39 |
| 394 | ARSI | NM_001012301.1 | 1.749 | 0.033 | 454.78 | 1071.58 |

TABLE 2-continued

Significant genes differentially expressed between fibroadenomas and *phyllodes* tumours.

| | Gene Name | Accession Number | Fold Change | q-value | Mean (FA) | Mean (PT) |
|---|---|---|---|---|---|---|
| 395 | LIMK2 | NM_001031801.1 | 0.577 | 0.033 | 3360.60 | 2217.09 |
| 396 | MIR758 | NR_030406.1 | 1.707 | 0.033 | 966.82 | 1948.64 |
| 397 | FAM19A3 | NM_182759.2 | 0.588 | 0.033 | 2991.35 | 1697.30 |
| 398 | EMILIN2 | NM_032048.2 | 1.669 | 0.033 | 861.14 | 1650.57 |
| 399 | MPL | NM_005373.1 | 0.614 | 0.033 | 4382.76 | 2621.58 |
| 400 | NCRNA00086 | NR_024359.1 | 0.624 | 0.033 | 4452.01 | 2848.11 |
| 401 | MAP7 | NM_003980.3 | 0.627 | 0.033 | 3641.58 | 2247.45 |
| 402 | PTPN14 | NM_005401.3 | 0.629 | 0.033 | 2264.16 | 1485.96 |
| 403 | C1orf210 | NM_182517.1 | 0.633 | 0.033 | 1642.61 | 993.86 |
| 404 | OGFRL1 | NM_024576.3 | 0.636 | 0.033 | 2972.37 | 2001.70 |
| 405 | UHRF1* | NM_013282.3 | 1.567 | 0.033 | 1799.98 | 3710.71 |
| 406 | FKBP5 | NM_004117.2 | 0.638 | 0.033 | 5802.11 | 3205.01 |
| 407 | MARVELD2 | NM_001038603.1 | 0.647 | 0.033 | 1859.90 | 1222.49 |
| 408 | AP3B2 | NM_004644.3 | 0.650 | 0.033 | 2544.13 | 1846.27 |
| 409 | LOXL1 | NM_005576.2 | 1.537 | 0.033 | 1546.19 | 3043.68 |
| 410 | SEMA6D | XM_932857.1 | 0.658 | 0.033 | 7387.83 | 4338.46 |
| 411 | LIMK2 | NM_016733.2 | 0.660 | 0.033 | 3146.77 | 2118.91 |
| 412 | WISP1 | NM_080838.1 | 1.507 | 0.033 | 595.66 | 1293.80 |
| 413 | PATE2 | NM_212555.1 | 2.069 | 0.034 | 723.49 | 1495.55 |
| 414 | GHR | NM_000163.2 | 0.547 | 0.034 | 5916.34 | 3780.11 |
| 415 | RIMS3 | NM_014747.2 | 0.557 | 0.034 | 2868.29 | 1445.12 |
| 416 | NCAM2 | NM_004540.2 | 1.745 | 0.034 | 568.60 | 1146.17 |
| 417 | IRF5 | NM_002200.3 | 0.574 | 0.034 | 6314.57 | 3417.46 |
| 418 | TNXB | NM_019105.5 | 0.578 | 0.034 | 4307.63 | 2506.85 |
| 419 | ESM1 | NM_007036.2 | 1.695 | 0.034 | 419.83 | 1125.72 |
| 420 | BCAM | NM_005581.3 | 0.592 | 0.034 | 4008.67 | 2717.16 |
| 421 | AGAP2 | NM_014770.2 | 1.678 | 0.034 | 597.65 | 1349.29 |
| 422 | FAM70A | NM_017938.2 | 0.599 | 0.034 | 1124.51 | 582.97 |
| 423 | KRTCAP3 | NM_173853.2 | 0.607 | 0.034 | 2644.96 | 1708.37 |
| 424 | SSTR2 | NM_001050.2 | 1.635 | 0.034 | 511.65 | 1311.88 |
| 425 | HISPPD2A | NM_014659.3 | 0.612 | 0.034 | 3479.15 | 2356.67 |
| 426 | NEBL | NM_213569.1 | 0.613 | 0.034 | 1967.93 | 1448.98 |
| 427 | EPHB2 | NM_017449.2 | 1.616 | 0.034 | 576.57 | 1112.69 |
| 428 | ARHGEF6 | NM_004840.2 | 0.626 | 0.034 | 4110.98 | 2539.33 |
| 429 | NDP | NM_000266.1 | 0.639 | 0.034 | 4433.51 | 2980.29 |
| 430 | RDH13 | NM_138412.2 | 0.641 | 0.034 | 2995.10 | 1913.10 |
| 431 | IL33 | NM_033439.2 | 0.649 | 0.034 | 2375.01 | 1504.68 |
| 432 | FBP1 | NM_000507.2 | 0.660 | 0.034 | 4784.64 | 2871.86 |
| 433 | CD52 | NM_001803.2 | 0.664 | 0.034 | 1743.20 | 1066.91 |
| 434 | COL4A3 | NM_000091.3 | 0.483 | 0.036 | 1440.44 | 719.66 |
| 435 | HAO2 | NM_001005783.1 | 1.840 | 0.036 | 700.28 | 1772.14 |
| 436 | DSC2 | NM_004949.2 | 0.615 | 0.036 | 1580.48 | 1016.66 |
| 437 | FLJ35220 | NM_173627.2 | 0.635 | 0.036 | 5574.31 | 3487.78 |
| 438 | TUBA4A | NM_006000.1 | 0.637 | 0.036 | 3251.36 | 2077.71 |
| 439 | RGS4 | NM_005613.3 | 1.567 | 0.036 | 2900.10 | 5683.53 |
| 440 | ALOX12P2 | NR_002710.2 | 0.660 | 0.036 | 2633.27 | 1640.38 |
| 441 | KLHL13 | NM_033495.2 | 0.661 | 0.036 | 3417.06 | 2333.31 |
| 442 | CBX2 | NM_032647.2 | 1.510 | 0.036 | 774.71 | 1569.19 |
| 443 | STARD13 | NM_178007.1 | 1.502 | 0.036 | 1304.35 | 2397.16 |
| 444 | PAX3 | NM_181457.1 | 2.324 | 0.039 | 597.99 | 2629.24 |
| 445 | ELF5 | NM_198381.1 | 0.507 | 0.039 | 3148.49 | 2175.22 |
| 446 | RASL10A | NM_001007279.1 | 0.565 | 0.039 | 8881.16 | 5468.29 |
| 447 | TUBB3 | NM_006086.2 | 1.706 | 0.039 | 4462.77 | 11205.60 |
| 448 | NCAPG | NM_022346.3 | 1.627 | 0.039 | 1297.34 | 3067.78 |
| 449 | STGC3 | NM_001006608.1 | 1.527 | 0.039 | 1036.13 | 1730.31 |
| 450 | MARVELD3 | NM_001017967.2 | 0.656 | 0.039 | 5956.64 | 3727.05 |
| 451 | PLCH2 | NM_014638.2 | 0.656 | 0.039 | 4228.64 | 2330.33 |
| 452 | SCGB2A1 | NM_002407.1 | 0.478 | 0.042 | 6748.52 | 2718.14 |
| 453 | MAG | NM_002361.2 | 0.483 | 0.042 | 3992.14 | 1543.57 |
| 454 | TNFRSF19 | NM_018647.2 | 1.857 | 0.042 | 487.79 | 1122.24 |
| 455 | PIWIL4 | NM_152431.1 | 1.722 | 0.042 | 926.50 | 1753.34 |
| 456 | THY1 | NM_006288.2 | 1.679 | 0.042 | 1530.80 | 3262.60 |
| 457 | ARL4A | NM_005738.2 | 0.597 | 0.042 | 1309.67 | 715.34 |
| 458 | C10orf81 | NM_024889.3 | 0.601 | 0.042 | 6115.98 | 3386.63 |
| 459 | ZYX | NM_003461.4 | 1.638 | 0.042 | 3139.48 | 5732.50 |
| 460 | ALPK1 | NM_025144.2 | 0.617 | 0.042 | 4443.17 | 2971.44 |
| 461 | TAC1 | NM_013996.1 | 1.613 | 0.042 | 750.93 | 1586.43 |
| 462 | FLJ41170 | NM_001004332.1 | 1.589 | 0.042 | 1979.78 | 3648.73 |
| 463 | NCF4 | NM_000631.3 | 0.630 | 0.042 | 4176.33 | 2724.81 |
| 464 | TSPAN13 | NM_014399.3 | 0.632 | 0.042 | 3535.54 | 2399.95 |
| 465 | JUP | NM_021991.1 | 0.658 | 0.042 | 1698.53 | 1040.23 |
| 466 | ZCCHC2 | NM_017742.3 | 0.665 | 0.042 | 5162.55 | 3490.08 |
| 467 | CIDEC | NM_022094.2 | 0.463 | 0.046 | 2205.13 | 941.07 |
| 468 | GAGE7 | NM_021123.1 | 2.110 | 0.046 | 575.07 | 5033.76 |

TABLE 2-continued

Significant genes differentially expressed between fibroadenomas and *phyllodes* tumours.

| | Gene Name | Accession Number | Fold Change | q-value | Mean (FA) | Mean (PT) |
|---|---|---|---|---|---|---|
| 469 | C12orf64 | NM_173591.1 | 0.550 | 0.046 | 1211.27 | 462.96 |
| 470 | PLA2G4F | NM_213600.2 | 0.554 | 0.046 | 2543.44 | 1380.16 |
| 471 | UBE2T | NM_014176.1 | 1.591 | 0.046 | 1266.30 | 2904.94 |
| 472 | HBB | NM_000518.4 | 0.637 | 0.046 | 3566.15 | 1765.02 |
| 473 | TMEM100 | NM_018286.1 | 1.537 | 0.046 | 256.03 | 836.57 |
| 474 | RPS6KA2 | NM_021135.4 | 0.655 | 0.046 | 8247.86 | 5568.94 |
| 475 | HAS2 | NM_005328.1 | 1.517 | 0.046 | 1035.99 | 2001.11 |
| 476 | GABPAP | XM_938298.1 | 1.506 | 0.046 | 598.04 | 1098.78 |
| 477 | PAX3 | NM_013942.2 | 2.142 | 0.049 | 537.16 | 2262.60 |
| 478 | SLC26A3 | NM_000111.1 | 0.482 | 0.049 | 4880.16 | 2852.26 |
| 479 | GAGE5 | NM_001475.1 | 2.062 | 0.049 | 759.23 | 5996.04 |
| 480 | SALL1 | NM_002968.1 | 1.951 | 0.049 | 1058.12 | 2064.68 |
| 481 | MCART6 | NM_001012755.1 | 1.882 | 0.049 | 945.35 | 1766.50 |
| 482 | BAPX1 | NM_001189.2 | 1.812 | 0.049 | 403.09 | 1134.67 |
| 483 | ST6GAL2 | NM_032528.1 | 1.780 | 0.049 | 831.75 | 2110.68 |
| 484 | PRODH | NM_016335.2 | 0.569 | 0.049 | 1709.93 | 1160.31 |
| 485 | CHST6 | NM_021615.3 | 1.752 | 0.049 | 658.88 | 1500.16 |
| 486 | SHOX2 | NM_006884.1 | 1.711 | 0.049 | 720.36 | 1506.59 |
| 487 | LY6H | XM_937329.1 | 1.685 | 0.049 | 1172.31 | 3856.24 |
| 488 | SNORD78 | NR_003944.1 | 1.657 | 0.049 | 520.12 | 1195.82 |
| 489 | ANGPT2 | NM_001118887.1 | 1.647 | 0.049 | 854.48 | 1785.14 |
| 490 | SLC5A1 | NM_000343.1 | 0.614 | 0.049 | 3000.44 | 1985.11 |
| 491 | PGLYRP2 | NM_052890.3 | 0.628 | 0.049 | 3602.18 | 2424.65 |
| 492 | MEG8 | NR_024149.1 | 1.586 | 0.049 | 1089.55 | 1969.35 |
| 493 | FGF1 | NM_033136.1 | 0.649 | 0.049 | 2508.60 | 1660.88 |
| 494 | DKK2 | NM_014421.2 | 0.650 | 0.049 | 1471.40 | 804.08 |
| 495 | TCIRG1 | NM_006053.2 | 1.522 | 0.049 | 1172.05 | 1991.77 |

*genes with primers successfully designed for qPCR assays

Example 3

Validation of Selected Genes by Quantitative Polymerase Chain Reaction (qPCR) Assay Primers Design Primers were designed using Primer-BLAST (NCBI) with accession number listed in Table 3. Criteria for qPCR primers designed were as follows: 1) amplicon size of 50 to 80 basepair (bp); 2) at least one primer spanning across an exon-exon boundary; 3) At least 7 bases must anneal to the 5' and 3' side of the junction. List of primers designed is as shown in Table 3.

TABLE 3

Primers designed for potential differentiating genes and normalization genes.

| Gene Name | Accession Number provided by WG-DASL | Accession number used for primer design | Forward Primer Sequence | Reverse Primer Sequence | Amplicon size |
|---|---|---|---|---|---|
| ABCA8 | NM_007168.2 | NM_007168.2 | CCT GGC GGA CAG GAA AGT ATT (SEQ ID NO: 3) | GAA GAG CCC GCG CAC TTT AG (SEQ ID NO: 4) | 57 |
| ADH1B | NM_000668.3 | NM_000668.5 | TCG CAT TAA GAT GGT GGC TGT (SEQ ID NO: 5) | CCA CGT GGT CAT CTG TGT GA (SEQ ID NO: 6) | 50 |
| ADH1C | NM_000669.3 | NM_000669.3 | GTT CGC ATT AAG ATG GTG GCT G (SEQ ID NO: 7) | GTT GCC ACT AAC CAC ATG CT (SEQ ID NO: 8) | 63 |
| APOD | NM_001647.2 | NM_001647.3 | CTG CAT CCA GGC CAA CTA CTC (SEQ ID NO: 9) | GTT CCA TCA GCT CTC AAC TCC T (SEQ ID NO: 10) | 78 |

TABLE 3-continued

Primers designed for potential differentiating genes and normalization genes.

| Gene Name | Accession Number provided by WG-DASL | Accession number used for primer design | Forward Primer Sequence | Reverse Primer Sequence | Amplicon size |
|---|---|---|---|---|---|
| C2orf40 | NM_032411.1 | NM_032411.2 | AAC GAG AAG CAC CTG TTC CAA (SEQ ID NO: 11) | GCT TTA TTC TCA TCA ACG GCC A (SEQ ID NO: 12) | 55 |
| CALML5 | NM_017422.3 | NM_017422.4 | GGC CCA GCT AAG GAA ACT CAT (SEQ ID NO: 13) | CTC CTG GAA GCT GAT TTC GC (SEQ ID NO: 14) | 67 |
| CCL19 | NM_006274.2 | NM_006274.2 | ACC TCA GCC AAG ATG AAG CG (SEQ ID NO: 15) | CCT CTG CAC GGT CAT AGG TT (SEQ ID NO: 16) | 51 |
| CH25H | NM_003956.2 | NM_003956.3 | ATG GAG TTC TTC GTG TGG CA (SEQ ID NO: 17) | CTT GTG GAA GGT GCG GTA CA (SEQ ID NO: 18) | 66 |
| CHST1 | NM_003654.2 | NM_003654.5 | CTC TTT GAC CTC ACC CCT TGG (SEQ ID NO: 19) | TTC CAG GAA CAT TGC ATG GC (SEQ ID NO: 20) | 66 |
| COL17A1 | NM_130778.1 | NM_000494.3 | CTT GCC GGG AAC CTC CTA TG (SEQ ID NO: 21) | AAT TCA GAC CCT CGC AGC AA (SEQ ID NO: 22) | 54 |
| CTHRC1 | NM_138455.2 | NM_138455.3 | GGT GGT GGA CCT GTA TAA TGG A (SEQ ID NO: 23) | GTC TCG ACC AGG CAC TCC T (SEQ ID NO: 24) | 61 |
| CYP1B1 | NM_000104.2 | NM_000104.3 | CTT CAC CAG GTA TCC TGA TGT GC (SEQ ID NO: 25) | CAT ACA AGG CAG ACG GTC CC (SEQ ID NO: 26) | 82 |
| DAPL1 | NM_001017920.1 | NM_001017920.2 | CGC ACT GGA GAA GCT CAA CTA (SEQ ID NO: 27) | GGG TTT TTG ATG CGC CAT GT (SEQ ID NO: 28) | 61 |
| DPYSL4 | NM_006426.1 | NM_006426.2 | GGA TCA CGA GTG ACC GCC TT (SEQ ID NO: 29) | TCG TCA TTC ACG ATC CTC CC (SEQ ID NO: 30) | 52 |
| FN1 | NM_212474.1 | NM_054034.2 | TCG CAG CTT CGA GAT CAG TG (SEQ ID NO: 31) | GAC GCT TGT GGA ATG TGT CG (SEQ ID NO: 32) | 70 |
| GAGE2B | NM_001098411.3 | NM_001098411.3 | TCA TCT GTG TGA AAT ATG AGT TGG (SEQ ID NO: 33) | GGC TCT ACG CTAG CGT CTT GG (SEQ ID NO: 34) | 71 |
| GCNT2 | NM_145649.2 | NM_001491.2 | CTG CCA CGG CCA CTA TGT A (SEQ ID NO: 35) | CCA GCC ACT TTA AGT CTC CGT (SEQ ID NO: 36) | 62 |
| GRB7 | NM_005310.2 | NM_001030002.2 | ACC TCT AAG GAT CCG AGG CA (SEQ ID NO: 37) | ACC ACG TAC ACG TTG GAC TC (SEQ ID NO: 38) | 65 |

TABLE 3-continued

Primers designed for potential differentiating genes and normalization genes.

| Gene Name | Accession Number provided by WG-DASL | Accession number used for primer design | Forward Primer Sequence | Reverse Primer Sequence | Amplicon size |
|---|---|---|---|---|---|
| HEPACAM2 | NM_198151.1 | NM_198151.1 | TTC CAG GAT TCC AAG CAG GT (SEQ ID NO: 39) | GCA AAT CTT GCC CCG ATA CAC (SEQ ID NO: 40) | 59 |
| HOXD13 | NM_000523.2 | NM_000523.3 | CTT CCT TTC CAG GGG ATG TGG (SEQ ID NO: 41) | CCC TCT TCG GTA GAC GCA C (SEQ ID NO: 42) | 59 |
| KIF15 | NM_020242.1 | NM_020242.2 | ATC TCA GGT TAG AAA ACG AAA AGC (SEQ ID NO: 43) | TAG GAA TCC TGT AGG CAG GC (SEQ ID NO: 44) | 58 |
| KIF20A | NM_005733.1 | NM_005733.2 | ACG ATT CAA GGT ACC ATC AAG GA (SEQ ID NO: 45) | ATT GAA GAT CAG CGC CAG GG (SEQ ID NO: 46) | 63 |
| LAMB1 | NM_002291.1 | NM_002291.2 | GCT TTC AGT TTC TTA GCC CTG TG (SEQ ID NO: 47) | CGC AGC CGT AGC TGA ACT (SEQ ID NO: 48) | 70 |
| LHX2 | NM_004789.3 | NM_004789.3 | AGT CGG AGC TCA CCT GTT TC (SEQ ID NO: 49) | AGA GAA GCG CCT GTA GTA GTC (SEQ ID NO: 50) | 71 |
| MMP3 | NM_002422.3 | NM_002422.3 | TGC AGT TAG AGA ACA TGG AGA CTT (SEQ ID NO: 51) | AGG CAT GGG CCA AAA CAT TTC (SEQ ID NO: 52) | 65 |
| NEFL | NM_006158.1 | NM_006158.4 | TTG CAG CTT ACA GGA AAC TCT TG (SEQ ID NO: 53) | CTG GTG AAA CTG AGT CGG GT (SEQ ID NO: 54) | 55 |
| NPTX2 | NM_002523.1 | NM_002523.2 | CTG GAG CGA GGC AAT AGC G (SEQ ID NO: 55) | GTG GGA GGG ACA CCT TGA AC (SEQ ID NO: 56) | 58 |
| OR5P3 | NM_153445.1 | NM_153445.1 | ATG GGG ACT GGA AAT GAC ACC (SEQ ID NO: 57) | ATC CTC AGA TAA CCC CAA AAG AGT (SEQ ID NO: 58) | 60 |
| PRAME | NM_206956.1 | NM_206955.1 | TCC AGA GAC AAC TTC GCG G (SEQ ID NO: 59) | CCA CGC ACG TCT GAG AGT AAT A (SEQ ID NO: 60) | 75 |
| RORC | NM_001001523.1 | NM_005060.3 | CCT GAC AGA GAT AGA GCA CCT G (SEQ ID NO: 61) | CCC TGT AGG ACT TGC AGA CG (SEQ ID NO: 62) | 50 |
| SCARA5 | NM_173833.3 | NM_173833.5 | TTC ATC TTA GCA GTG TCC AGG C (SEQ ID NO: 63) | GTT CAC ATT GCG AGT CAG GG (SEQ ID NO: 64) | 69 |
| SERHL2 | NM_014509.3 | NM_014509.4 | CCT CTT CTC CCG CAA GAC TTT TA (SEQ ID NO: 65) | CTG TAA TGG GAC GAG AGC CC (SEQ ID NO: 66) | 71 |

TABLE 3-continued

Primers designed for potential differentiating genes and normalization genes.

| Gene Name | Accession Number provided by WG-DASL | Accession number used for primer design | Forward Primer Sequence | Reverse Primer Sequence | Amplicon size |
|---|---|---|---|---|---|
| SHISA2 | NM_001007538.1 | NM_001007538.1 | TCG GCA GTG CCC ATC TAC G (SEQ ID NO: 67) | ACA AAC ACG GAG CCA ACA ATG (SEQ ID NO: 68) | 50 |
| SPAG11 B | XM_943161.1 | NM_016512.3 | TAC CAA GTG CAC ATC TCT CAC C (SEQ ID NO: 69) | AGG CCC TAA AAA GTC CAC ACA (SEQ ID NO: 70) | 72 |
| SPC25 | NM_020675.3 | NM_020675.3 | CCT GCC TGC GAA GCA TTG TC (SEQ ID NO: 71) | TCG AAA AGT GCC AGT TCG TCC (SEQ ID NO: 72) | 56 |
| SYNGAP1 | NM_006772.1 | NM_006772.2 | GCC CCC TTC AGA GAT GTA CG (SEQ ID NO: 73) | ACG TAT TGG GTT CGG TGC AT (SEQ ID NO: 74) | 50 |
| TESC | NM_017899.1 | NM_017899.3 | TGT TCC ACA TGT ACG ACT CGG (SEQ ID NO: 75) | GCT CCT CGA CCA CAT TTC GAT (SEQ ID NO: 76) | 72 |
| TP63_v1* | NM_001114979.1 | NM_001114979.1 | AGC AGC AAG TTT CGG ACA GT (SEQ ID NO: 77) | CGA AAC GGG CGC TTC GTA (SEQ ID NO: 78) | 55 |
| TP63_v2* | NM_001114981.1 | NM_001114981.1 | ATT GCA GCA TTG TCA GGA TCT GG (SEQ ID NO: 79) | GAT CGC ATG TCG AAA TTG CTC A (SEQ ID NO: 80) | 61 |
| TRERF1 | NM_033502.1 | NM_033502.2 | AGG AGT GTG GCA AAG TCT TCT T (SEQ ID NO: 81) | CTC CTG CTG CCT GTG AGT TT (SEQ ID NO: 82) | 71 |
| TRIM29 | NM_012101.2 | NM_012101.3 | AAG CAG ACT ATG CTG TCT CAC T (SEQ ID NO: 83) | ATC CCG TTG CCT TTG TTG AC (SEQ ID NO: 84) | 56 |
| UBE2C | NM_181800.1 | NM_007019.3 | GGC AAA AGG CTA CAG CAG GA (SEQ ID NO: 85) | TCA GGG AAG GCA GAA ATC CC (SEQ ID NO: 86) | 71 |
| UHRF1 | NM_013282.2 | NM_013282.3 | TAC GAC GAC TAC CCG GAG AA (SEQ ID NO: 87) | GGA CGT CCC TGG AGT CAT C (SEQ ID NO: 88) | 52 |
| RMRP† | NR_003051.2 | NR_003051.3 | CAG AGA GTG CCA CGT GCA TA (SEQ ID NO: 89) | TAC GCT TCT TGG CGG ACT TT (SEQ ID NO: 90) | 70 |
| RPL18† | NM_000979.2 | NM_000979.3 | AGA GGT GTA CCG GCA TTT CG (SEQ ID NO: 91) | GTA GGG TTT GGT GTG GCT GT (SEQ ID NO: 92) | 61 |
| RPLP2† | NM_001004.2 | NM_001004.3 | ACC GGC TCA ACA AGG TTA TCA (SEQ ID NO: 93) | CTG GGA AAT GAC GTC TTC AA (SEQ ID NO: 94) | 62 |

TABLE 3-continued

Primers designed for potential differentiating genes and normalization genes.

| Gene Name | Accession Number provided by WG-DASL | Accession number used for primer design | Forward Primer Sequence | Reverse Primer Sequence | Amplicon size |
|---|---|---|---|---|---|
| SNORA6 1† | NR_002987.1 | NR_002987.1 | TCC TGA TCC CTT TCC CAT CG (SEQ ID NO: 95) | TCC TCC TTT TAC GAC CAC CA (SEQ ID NO: 96) | 57 |
| SNORA4 5† | NR_002977.1 | NR_002977.1 | CTT GTC CTG GTG TGC TAG AGT (SEQ ID NO: 97) | CCC CCA CCA GTG AAT CAA GA (SEQ ID NO: 98) | 61 |

*refers to different variants of the same gene
†normalization genes

Synthesis of cDNA and qPCR Assay cDNA was synthesized from 1 μg of RNA using the High Capacity cDNA Reverse Transcription Kit (Applied Biosystems®, Life Technologies, USA) on a thermal cycler according to manufacturer's protocol. cDNA was then diluted 10-fold for subsequent qPCR assays.

qPCR assays were performed on the CFX96 machine. Each qPCR reaction consisted of 1× Power SYBR® Green PCR Master Mix (Life Technologies, USA), 0.5 μM of forward and reverse primer each and 1 μl of the diluted cDNA as template in a final total volume of 10 μl. Non-template control acted as a negative control. Specificity of the amplicons was checked with meltcurve analysis.

To validate the expression observed on the WG-DASL Array, six representative samples were used as a pilot run for each potential gene tested.

Data Analysis

Expression data from qPCR assays was obtained in terms of threshold cycle (Ct). Ct above 40 was deemed as below limit of detection and is converted to 40. Delta Ct (ΔCt) was quantified as follows:

ΔCt of test gene=Ct−geometric mean (Ct of five normalization genes)

ΔCt data was transformed to $2^{-\Delta Ct}$ as a positive linear scale for comparison with expression value of DASL. Significance of correlation was analyzed with Pearson's correlation test. Table 4 shows the results of the pilot run. Genes with good correlation value (r≥0.6) were subjected to testing on remaining 40 samples. Two samples had no sufficient RNA for the qPCR assays after characterization on WG-DASL and hence were not included in the analysis.

TABLE 4

Correlation of expression value on WG-DASL and qPCR results for genes selected.

| Gene Name | Pearson's r | p-value |
|---|---|---|
| PRAME* | 0.991 | <0.001 |
| ADH1B* | 0.976 | 0.001 |
| CTHRC1* | 0.968 | 0.002 |
| NPTX2* | 0.965 | 0.002 |
| NEFL* | 0.961 | 0.002 |
| ABCA8* | 0.931 | 0.007 |
| DAPL1* | 0.915 | 0.011 |
| TP63_v2* | 0.901 | 0.014 |

TABLE 4-continued

Correlation of expression value on WG-DASL and qPCR results for genes selected.

| Gene Name | Pearson's r | p-value |
|---|---|---|
| COL17A1* | 0.896 | 0.016 |
| GCNT2* | 0.880 | 0.021 |
| CCL19* | 0.870 | 0.024 |
| MMP3* | 0.855 | 0.030 |
| FN1* | 0.835 | 0.039 |
| TRERF1* | 0.798 | 0.057 |
| TRIM29* | 0.794 | 0.059 |
| TESC* | 0.777 | 0.069 |
| KIF20A* | 0.776 | 0.070 |
| UHRF1* | 0.739 | 0.093 |
| HEPACAM2* | 0.714 | 0.111 |
| APOD* | 0.713 | 0.112 |
| SERHL2* | 0.671 | 0.145 |
| KIF15* | 0.659 | 0.154 |
| HOXD13* | 0.625 | 0.185 |
| GAGE2B | 0.557 | 0.251 |
| CALML5 | 0.548 | 0.260 |
| C2orf40 | 0.545 | 0.263 |
| ADH1C | 0.487 | 0.327 |
| CYP1B1 | 0.442 | 0.380 |
| SPAG11B | 0.438 | 0.385 |
| GRB7 | 0.411 | 0.418 |
| UBE2C | 0.336 | 0.580 |
| SYNGAP1 | 0.330 | 0.524 |
| TP63_v1 | 0.220 | 0.676 |
| LAMB1 | 0.188 | 0.762 |
| OR5P3 | 0.082 | 0.877 |
| SPC25 | 0.056 | 0.928 |
| SHISA2 | −0.006 | 0.991 |
| SCARA5 | −0.052 | 0.922 |
| LHX2 | −0.103 | 0.846 |
| RORC | −0.157 | 0.766 |
| DPYSL4 | −0.201 | 0.703 |
| CH25H | −0.298 | 0.566 |
| CHST1 | −0.844 | 0.072 |

*genes selected for full-scale run on 40 samples

Example 4

Development of an Algorithm Model Based on qPCR Assay Results on 46 Samples

Variable Selection Using Random Forest

Figure 2:
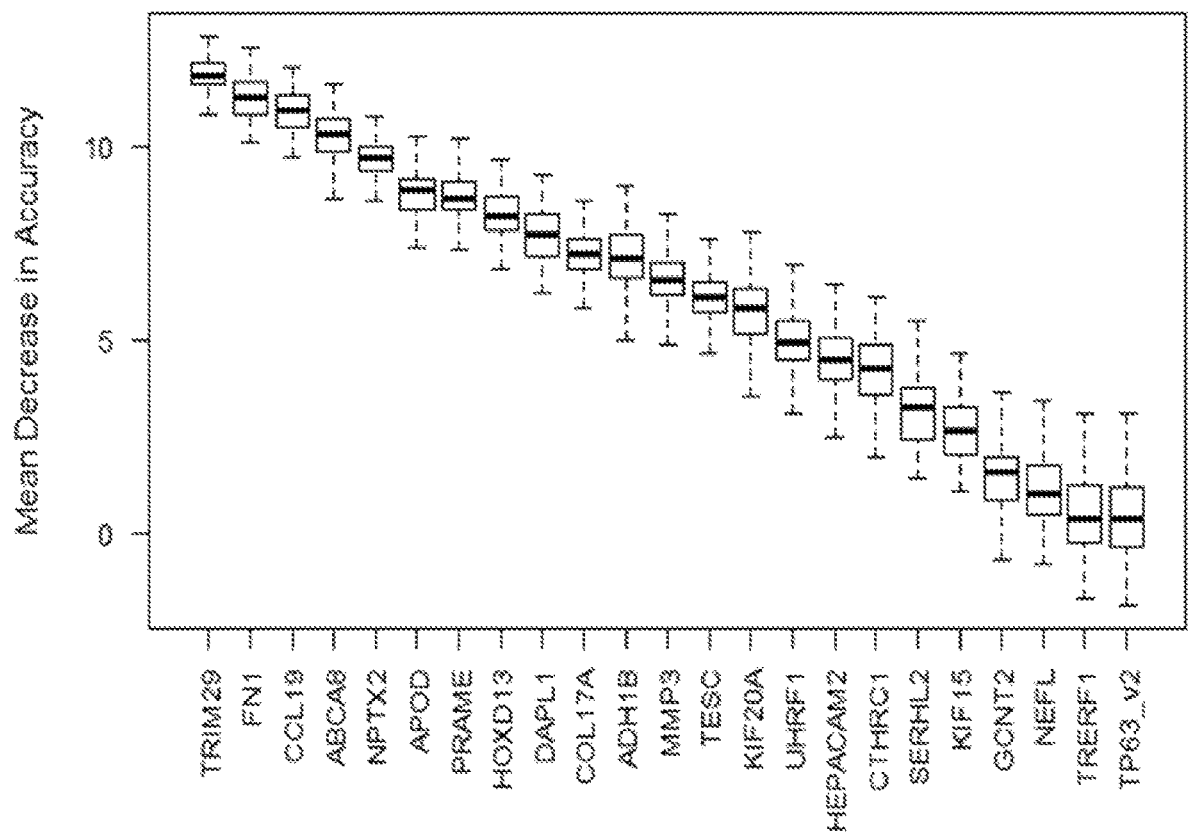
FIG. 2. Boxplot of mean decrease in accuracy for 100 RF trees generated for each gene. ΔCt values of all 23 genes on 46 samples were analysed with Random Forest (RF) classifier algorithm (R version) to rank the importance of genes differentiating fibroadenomas and phyllodes tumours. Mean decrease in accuracy measures the importance of each gene to the classification.

ΔCt values of all 23 genes on 46 samples were analyzed with Random Forest (RF) classifier algorithm (R version) to rank importance of genes differentiating fibroadenomas and phyllodes tumours. Results are as shown in FIG. 2 for 100 RF trees generated.

Development of an Algorithm Model Using Logistic Regression

Top seven genes (TRIM29, FN1, CCL19, ABCA8, NPTX2, APOD, PRAME) were used for logistic regression modeling. All possible models were screened to find the best model using the glmulti package (R version) including the interactions terms. The best model was selected based on the lowest AIC (Akaike information criteria) value. The coefficient of the best model generated is as shown in Table 5. The AIC for the model was 14.2.

TABLE 5

Coefficients of the best model in predicting diagnosis in the 46-sample set.

| Genes | Coefficients |
| --- | --- |
| APOD | 2.95575 |
| APOD: ABCA8 | −0.11934 |
| PRAME: FN1 | −0.43165 |
| PRAME: CCL19 | 0.08326 |

Example 5

Validation of the Predicting Algorithm on an Independent Set

An independent set of 230 core biopsy samples (189 fibroadenomas and 41 phyllodes tumours) was employed to evaluate the performance of the algorithm. RNA was extracted and cDNA synthesized as per the protocol above. ΔCt values were obtained as per the protocols above. Probability (p) of each sample whether it is a fibroadenoma or phyllodes tumours are calculated in the following manner:

$$p = \frac{e^{2.95575(\Delta Ct\ of\ APOD)-0.11934(\Delta Ct\ of\ APOD*\Delta Ct\ of\ ABCA8)-0.43165(\Delta Ct\ of\ PRAME*\Delta Ct\ of\ FN1)+0.08326(\Delta Ct\ of\ PRAME*\Delta Ct\ of\ CCL19)}}{1 + e^{2.95575(\Delta Ct\ of\ APOD)-0.11934(\Delta Ct\ of\ APOD*\Delta Ct\ of\ ABCA8)-0.43165(\Delta Ct\ of\ PRAME*\Delta Ct\ of\ FN1)+0.08326(\Delta Ct\ of\ PRAME*\Delta Ct\ of\ CCL19)}}$$

Figures 3A, 3B:
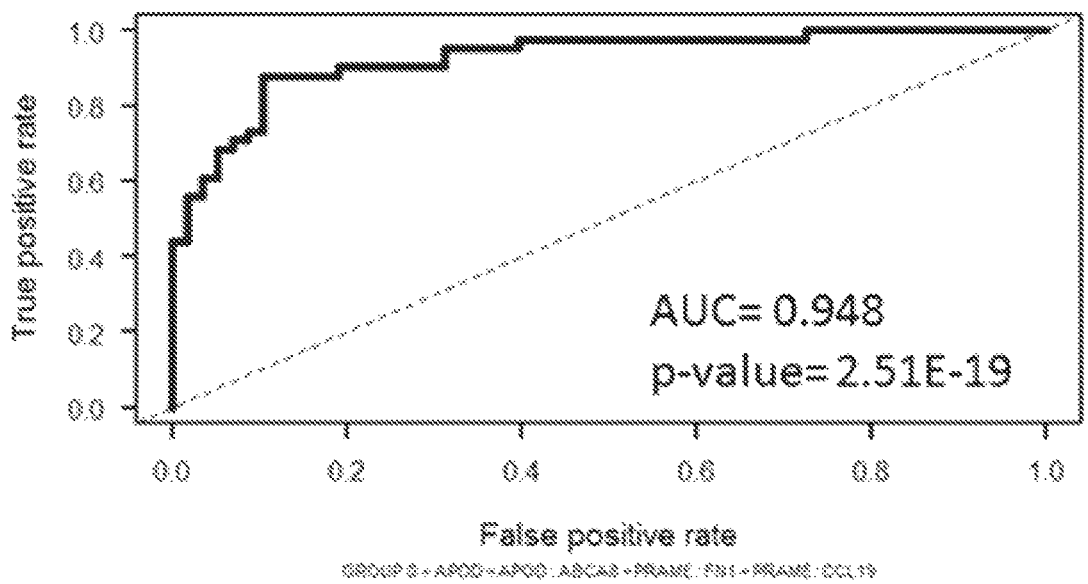
FIG. 3. Performance of the algorithm in predicting diagnosis in the independent set of 230 core biopsies. (A) the algorithm has sensitivity of 94.7% and specificity of 82.9%. The positive predictive value (PPV) of the algorithm is 77.3% and the negative predictive value (NPV) of the algorithm is 96.2%. (B) ROC curve of the performance of the algorithm on independent set of 230 core biopsies.

A sample is predicted as a phyllodes tumour when p is 0.5 and above. Otherwise, the sample is predicted as a fibroadenoma. The outcome of the multigene assay was compared against the final diagnosis on the corresponding surgical excisions. Cases without subsequent surgical excisions were free from progression for at least two years and diagnosis made based on the initial core biopsy was used as the reference instead. The five-gene assay has an overall accuracy of 92.6% (FIG. 3), with a sensitivity of 82.9% and specificity of 94.7%. The positive predictive value (PPV) and negative predictive value (NPV) are 77.3% and 96.2%.

Example 6

Protocol for a Multigene Assay Classifying Breast Fibroepithelial Lesion

Equipment
1. Real-time PCR machine
2. Nanodrop Spectrophotometer
3. Heat block/Water bath/Thermomixer
4. Microtome Materials
1. RNeasy FFPE Kit (Qiagen, Catalogue No. 73504)
2. Power SYBR®Green RNA-to-CT™ 1-Step Kit (Applied Biosystems®, Catalog No. 4389986)
3. Xylene
4. Absolute ethanol Consumables
1. 1.5 ml and 2.0 ml microtubes
2. Glass slides
3. Sterile scalpels Protocol
1. Identification of tumour area by a pathologist. Fish 5 sections of 10 μm of tissue onto 5 glass slides respectively.
2. Deparaffinise tissue in two changes of xylene and 3 changes of absolute ethanol. Scrape tumour area with a sterile scalpel and transfer tissue into a 1.5 ml microtube containing 500 μl absolute ethanol. Perform RNA extraction using Qiagen RNeasy FFPE Kit.
3. Quantify RNA with a Nanodrop Spectrophotometer.
4. For each well, prepare a 10 μl reaction as follows in Table 6 (table modified from Power SYBR® Green RNA-to-CT™ 1-Step Kit protocol). For non-template control (NTC), RNA template should be replaced by RNase-free water. Primer sequences are shown in Table 8.
5. Real-time PCR machine is set up as follows in Table 7 (table modified from Power SYBR® Green RNA-to-CT™ 1-Step Kit Protocol).
6. Check the meltcurve temperature (refer to Table 8) to ensure the desired product is amplified. Read Ct for each well for ABCA8, APOD, CCL19, FN1 and FRAME. Perform quantification for each well as follows:

ΔCt of each gene=Ct−geometric mean (Ct of RMRP, RPL18, RPLP2, SNORA45 and SNORA61)

7. Perform calculation as follow to work out a probability score.

$$p = \frac{e^{2.95575(\Delta Ct\ of\ APOD)-0.11934(\Delta Ct\ of\ APOD*\Delta Ct\ of\ ABCA8)-0.43165(\Delta Ct\ of\ PRAME*\Delta Ct\ of\ FN1)+0.08326(\Delta Ct\ of\ PRAME*\Delta Ct\ of\ CCL19)}}{1 + e^{2.95575(\Delta Ct\ of\ APOD)-0.11934(\Delta Ct\ of\ APOD*\Delta Ct\ of\ ABCA8)-0.43165(\Delta Ct\ of\ PRAME*\Delta Ct\ of\ FN1)+0.08326(\Delta Ct\ of\ PRAME*\Delta Ct\ of\ CCL19)}}$$

8. If p is 0.5 and above, the outcome of the test is a phyllodes tumour. If p is less than 0.5, the outcome of the test is a fibroadenoma.

TABLE 6

PCR reaction components

| Component | Volume (μl) |
| --- | --- |
| Power Sybr Green RT-PCR Mix (2x) | 5 |
| Forward and Reverse Primers* (200 nM) | 2 |

TABLE 6-continued

PCR reaction components

| Component | Volume (µl) |
|---|---|
| RT Enzyme Mix (125x) | 0.08 |
| RNase-free water | Variable |
| RNA template (100 ng) | Variable |

TABLE 7

Thermal cycling conditions for real-time PCR.

| Step | Temperature (° C.) | Time | Step |
|---|---|---|---|
| Reverse Transcription | 48 | 30 minutes | Reverse Transcription |
| Activation of DNA polymerase | 95 | 10 minutes | Activation of DNA polymerase |
| Cycling (40 cycles) | | | Cycling (40 cycles) |
| Denature | 95 | 15 seconds | Denature |
| Anneal/Extend | 60 | 60 seconds | Anneal/Extend |

TABLE 8

Primer sequences and meltcurve temperature.

| Name | Forwards Sequence | Reverse Sequence | Meltcurve Temperature (° C.) |
|---|---|---|---|
| ABCA8 | CCT GGC GGA CAG GAA AGT ATT (SEQ ID NO: 3) | GAA GAG CCC GCG CAC TTT AG (SEQ ID NO: 4) | 77.5 |
| APOD | CTG CAT CCA GGC CAA CTA CTC (SEQ ID NO: 9) | GTT CCA TCA GCT CTC AAC TCC T (SEQ ID NO: 10) | 75.5 |
| CCL19 | ACC TCA GCC AAG ATG AAG CG (SEQ ID NO: 15) | CCT CTG CAC GGT CAT AGG TT (SEQ ID NO: 16) | 77.5 |
| FN1 | TCG CAG CTT CGA GAT CAG TG (SEQ ID NO: 31) | GAC GCT TGT GGA ATG TGT CG (SEQ ID NO: 32) | 76 |
| PRAME | TCC AGA GAC AAC TTC GCG G (SEQ ID NO: 59) | CCA CGC ACG TCT GAG AGT AAT A (SEQ ID NO: 60) | 75.5 |
| RMRP | CAG AGA GTG CCA CGT GCA TA (SEQ ID NO: 89) | TAC GCT TCT TGG CGG ACT TT (SEQ ID NO: 90) | 80 |
| RPL18 | AGA GGT GTA CCG GCA TTT CG (SEQ ID NO: 91) | GTA GGG TTT GGT GTG GCT GT (SEQ ID NO: 92) | 81 |
| RPLP2 | ACC GGC TCA ACA AGG TTA TCA (SEQ ID NO: 93) | CTG GGC AAT GAC GTC TTC AA (SEQ ID NO: 94) | 75 |
| SNORA45 | CTT GTC CTG GTG TGC AGT (SEQ ID NO: 97) | CCC CCA CCA GTG AAT CAA GA (SEQ ID NO: 98) | 76 |
| SNORA61 | TCC TGA TCC CTT TCC CAT CG (SEQ ID NO: 95) | TCC TCC TTT TAC GAC CAC CA (SEQ ID NO: 96) | 75.5 |

What is claimed is:

1. A method of determining the type of fibroepithelial tumor of the breast, in a biological sample obtained from a patient in vitro or a method of managing the treatment of a patient with a fibroepithelial tumor of the breast, comprising:
   measuring the expression levels of a combination of genes comprising PRAME, ABCA8, CCL19, FN1, and APOD and obtaining an expression profile of the combination of genes in said sample;
   measuring the expression level of one or more normalized genes and obtaining an expression profile of the one or more normalized genes for use as a control;
   determining the differential activity of PRAME, ABCA8, CCL19, FN1 and APOD relative to the control based on the expression profile of the one or more genes and one or more normalized genes;
   correlating the differential activity PRAME, ABCA8, CCL19, FN1 and APOD relative to the control to determine a p-score using a predictive algorithm, wherein the predictive algorithm is:

$$p = \frac{e^{2.95575(\Delta Ct\ of\ APOD)-0.11934(\Delta Ct\ of\ APOD*\Delta Ct\ of\ ABCA8)-0.43165(\Delta Ct\ of\ PRAME*\Delta Ct\ of\ FN1)+0.08326(\Delta Ct\ of\ PRAME*\Delta Ct\ of\ CCL19)}}{1+e^{2.95575(\Delta Ct\ of\ APOD)-0.11934(\Delta Ct\ of\ APOD*\Delta Ct\ of\ ABCA8)-0.43165(\Delta Ct\ of\ PRAME*\Delta Ct\ of\ FN1)+0.08326(\Delta Ct\ of\ PRAME*\Delta Ct\ of\ CCL19)}};$$

determining the presence of a phyllodes tumor in the patient wherein the p-score is 0.5 and above; and
   treating patient for a phyllodes tumor.

2. The method of claim 1, wherein the one or more normalized genes are selected from the group consisting of RMRP, RPL18, RPLP2, SNORA61, and SNORA45.

3. The method of claim 1, wherein the one or more normalized genes consist of RMRP, RPL18, RPLP2, SNORA61, and SNORA45.

4. The method of claim 1, wherein the biological sample is selected from the group consisting of an organ, tissue, fraction, and a cell.

5. The method of claim 1, wherein the biological sample is a malignant tumor sample.

6. The method of claim 1, wherein the biological sample is a benign tumor sample.

7. The method of claim 5, wherein the tumor sample is a breast sample.

8. The method of claim 1, further comprising extracting RNA from the sample for measuring the expression level and obtaining the expression profile of the one or more genes and one or more normalized genes.

9. The method of claim 1, wherein the expression profile of the one or more genes and one or more normalized genes is obtained from the same biological sample.

10. The method of claim 8, wherein the expression profile of the one or more genes and one or more normalized genes is obtained by a quantitative PCR method.

11. A kit for determining the type of fibroepithelial tumor of the breast, in a biological sample in vitro, comprising:
    a primer pair for amplifying each of the genes in the combination of genes comprising PRAME, ABCA8, CCL19, FN1 and APOD; and
    a primer pair for amplifying each of one or more normalized genes selected from the group consisting of RMRP, RPL18, RPLP2, SNORA61, and SNORA45.

12. The kit of claim 11, wherein the combination of genes further comprises one or more genes selected from the group consisting of TRIM29, and NPTX2.

13. The kit of claim 11, wherein the one or more normalized genes consists of RMRP, RPL18, RPLP2, SNORA61, and SNORA45.

* * * * *

SEQUENCE LISTING

<160> NUMBER OF SEQ ID NOS: 98

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
cacttgggga cagcatgag                                                 19

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2 taacccettg gttgtgcat                                                 19

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
cctggcggac aggaaagtat t                                              21

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gaagagcccg cgcactttag                                                20

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
tcgcattaag atggtggctg t                                              21

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ccacgtggtc atctgtgtga                                                20

<210> SEQ ID NO 7
<211> LENGTH: 22
<212> TYPE: DNA
<213> ORGANISM: Artificial Sequence

```
<220> FEATURE:
<223> OTHER INFORMATION: Primer

<400> SEQUENCE: 7
gttcgcatta agatggtggc tg                                              22

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gttgccacta accacatgct                                                 20

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
ctgcatccag gccaactact c                                               21

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
gttccatcag ctctcaactc ct                                              22

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
aacgagaagc acctgttcca a                                               21

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gctttattct catcaacggc ca                                              22

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
ggcccagcta aggaaactca t                                               21
```

```
<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ctcctggaag ctgatttcgc                                              20

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
acctcagcca agatgaagcg                                              20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
cctctgcacg gtcataggtt                                              20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
atggagttct tcgtgtggca                                              20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
cttgtggaag gtgcggtaca                                              20

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
ctctttgacc tcaccccttg g                                            21

<210> SEQ ID NO 20
<211> LENGTH: 20
<212> TYPE: DNA
<213> ORGANISM: Artificial Sequence
<220> FEATURE:
<223> OTHER INFORMATION: Primer
```

<400> SEQUENCE: 20
ttccaggaac attgcatggc                                                          20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
cttgccggga acctcctatg                                                          20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
aattcagacc ctcgcagcaa                                                          20

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
ggtggtggac ctgtataatg ga                                                       22

<210> SEQ ID NO 24
<211> LENGTH: 19
<212> TYPE: DNA
<213> ORGANISM: Artificial Sequence
<220> FEATURE:
<223> OTHER INFORMATION: Primer

<400> SEQUENCE: 24
gtctcgacca ggcactcct                                                           19

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
cttcaccagg tatcctgatg tgc                                                      23

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
catacaaggc agacggtccc                                                          20

<210> SEQ ID NO 27

```
<211> LENGTH: 21
<212> TYPE: DNA
<213> ORGANISM: Artificial Sequence
<220> FEATURE:
<223> OTHER INFORMATION: Primer

<400> SEQUENCE: 27
cgcactggag aagctcaact a                                              21

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
gggtttttga tgcgccatgt                                                20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
ggatcacgag tgaccgcctt                                                20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tcgtcattca cgatcctccc                                                20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tcgcagcttc gagatcagtg                                                20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gacgcttgtg gaatgtgtcg                                                20

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
```

-continued

```
tcatctgtgt gaaatatgag ttggc                                              25

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
ggctctacgt agcgtcttgg                                                    20

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35
ctgccacggc cactatgta                                                     19

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
ccagccactt taagtctccg t                                                  21

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
acctctaagg atccgaggca                                                    20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
accacgtaca cgttggactc                                                    20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
ttccaggatt ccaagcaggt                                                    20

<210> SEQ ID NO 40
<211> LENGTH: 21
<212> TYPE: DNA
```

```
<213> ORGANISM: Artificial Sequence
<220> FEATURE:
<223> OTHER INFORMATION: Primer

<400> SEQUENCE: 40
gcaaatcttg ccccgataca c                                              21

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
cttcctttcc aggggatgtg g                                              21

<210> SEQ ID NO 42
<211> LENGTH: 19
<212> TYPE: DNA
<213> ORGANISM: Artificial Sequence
<220> FEATURE:
<223> OTHER INFORMATION: Primer

<400> SEQUENCE: 42
ccctcttcgg tagacgcac                                                 19

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
atctcaggtt agaaaacgaa aagc                                           24

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
taggaatcct gtaggcaggc                                                20

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
acgattcaag gtaccatcaa gga                                            23

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
attgaagatc agcgccaggg                                                20
```

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
gctttcagtt tcttagccct gtg                                    23

<210> SEQ ID NO 48
<211> LENGTH: 18
<212> TYPE: DNA
<213> ORGANISM: Artificial Sequence
<220> FEATURE:
<223> OTHER INFORMATION: Primer

<400> SEQUENCE: 48
cgcagccgta gctgaact                                          18

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
agtcggagct cacctgtttc                                        20

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
agagaagcgc ctgtagtagt c                                      21

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
tgcagttaga gaacatggag actt                                   24

<210> SEQ ID NO 52
<211> LENGTH: 21
<212> TYPE: DNA
<213> ORGANISM: Artificial Sequence
<220> FEATURE:
<223> OTHER INFORMATION: Primer

<400> SEQUENCE: 52
aggcatgggc caaaacattt c                                      21

<210> SEQ ID NO 53
<211> LENGTH: 23
<212> TYPE: DNA
<213> ORGANISM: Artificial Sequence
<220> FEATURE:

<223> OTHER INFORMATION: Primer

<400> SEQUENCE: 53
ttgcagctta caggaaactc ttg                                    23

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
ctggtgaaac tgagtcgggt                                        20

<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55
ctggagcgag gcaatagcg                                         19

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
gtgggaggga caccttgaac                                        20

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
atggggactg gaaatgacac c                                      21

<210> SEQ ID NO 58
<211> LENGTH: 24
<212> TYPE: DNA
<213> ORGANISM: Artificial Sequence
<220> FEATURE:
<223> OTHER INFORMATION: Primer

<400> SEQUENCE: 58
atcctcagat aacccaaaa gagt                                    24

<210> SEQ ID NO 59
<211> LENGTH: 19
<212> TYPE: DNA
<213> ORGANISM: Artificial Sequence
<220> FEATURE:
<223> OTHER INFORMATION: Primer

<400> SEQUENCE: 59
tccagagaca acttcgcgg                                         19

```
<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
ccacgcacgt ctgagagtaa ta                                              22

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
cctgacagag atagagcacc tg                                              22

<210> SEQ ID NO 62
<211> LENGTH: 20
<212> TYPE: DNA
<213> ORGANISM: Artificial Sequence
<220> FEATURE:
<223> OTHER INFORMATION: Primer

<400> SEQUENCE: 62
ccctgtagga cttgcagacg                                                 20

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63
ttcatcttag cagtgtccag gc                                              22

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
gttcacattg cgagtcaggg                                                 20

<210> SEQ ID NO 65
<211> LENGTH: 23
<212> TYPE: DNA
<213> ORGANISM: Artificial Sequence
<220> FEATURE:
<223> OTHER INFORMATION: Primer

<400> SEQUENCE: 65
cctcttctcc cgcaagactt tta                                             23

<210> SEQ ID NO 66
<211> LENGTH: 20
<212> TYPE: DNA
<213> ORGANISM: Artificial Sequence
<220> FEATURE:
<223> OTHER INFORMATION: Primer
```

```
<400> SEQUENCE: 66
ctgtaatggg acgagagccc                                               20

<210> SEQ ID NO 67
<211> LENGTH: 19
<212> TYPE: DNA
<213> ORGANISM: Artificial Sequence
<220> FEATURE:
<223> OTHER INFORMATION: Primer

<400> SEQUENCE: 67
tcggcagtgc ccatctacg                                                19

<210> SEQ ID NO 68
<211> LENGTH: 21
<212> TYPE: DNA
<213> ORGANISM: Artificial Sequence
<220> FEATURE:
<223> OTHER INFORMATION: Primer

<400> SEQUENCE: 68
acaaacacgg agccaacaat g                                             21

<210> SEQ ID NO 69
<211> LENGTH: 22
<212> TYPE: DNA
<213> ORGANISM: Artificial Sequence
<220> FEATURE:
<223> OTHER INFORMATION: Primer

<400> SEQUENCE: 69
taccaagtgc acatctctca cc                                            22

<210> SEQ ID NO 70
<211> LENGTH: 21
<212> TYPE: DNA
<213> ORGANISM: Artificial Sequence
<220> FEATURE:
<223> OTHER INFORMATION: Primer

<400> SEQUENCE: 70
aggccctaaa aagtccacac a                                             21

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
cctgcctgcg aagcattgtc                                               20

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72
tcgaaaagtg ccagttcgtc c                                             21

<210> SEQ ID NO 73
<211> LENGTH: 20
```

```
<212> TYPE: DNA
<213> ORGANISM: Artificial Sequence
<220> FEATURE:
<223> OTHER INFORMATION: Primer

<400> SEQUENCE: 73 gccccctttca gagatgtacg                                              20

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
acgtattggg ttcggtgcat                                               20

<210> SEQ ID NO 75
<211> LENGTH: 21
<212> TYPE: DNA
<213> ORGANISM: Artificial Sequence
<220> FEATURE:
<223> OTHER INFORMATION: Primer

<400> SEQUENCE: 75
tgttccacat gtacgactcg g                                             21

<210> SEQ ID NO 76
<211> LENGTH: 21
<212> TYPE: DNA
<213> ORGANISM: Artificial Sequence
<220> FEATURE:
<223> OTHER INFORMATION: Primer

<400> SEQUENCE: 76
gctcctcgac cacatttcga t                                             21

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
agcagcaagt ttcggacagt                                               20

<210> SEQ ID NO 78
<211> LENGTH: 18
<212> TYPE: DNA
<213> ORGANISM: Artificial Sequence
<220> FEATURE:
<223> OTHER INFORMATION: Primer

<400> SEQUENCE: 78
cgaaacgggc gcttcgta                                                 18

<210> SEQ ID NO 79
<211> LENGTH: 23
<212> TYPE: DNA
<213> ORGANISM: Artificial Sequence
<220> FEATURE:
<223> OTHER INFORMATION: Primer

<400> SEQUENCE: 79
```

```
attgcagcat tgtcaggatc tgg                                              23

<210> SEQ ID NO 80
<211> LENGTH: 22
<212> TYPE: DNA
<213> ORGANISM: Artificial Sequence
<220> FEATURE:
<223> OTHER INFORMATION: Primer

<400> SEQUENCE: 80
gatcgcatgt cgaaattgct ca                                               22

<210> SEQ ID NO 81
<211> LENGTH: 22
<212> TYPE: DNA
<213> ORGANISM: Artificial Sequence
<220> FEATURE:
<223> OTHER INFORMATION: Primer

<400> SEQUENCE: 81
aggagtgtgg caaagtcttc tt                                               22

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
ctcctgctgc ctgtgagttt                                                  20

<210> SEQ ID NO 83
<211> LENGTH: 22
<212> TYPE: DNA
<213> ORGANISM: Artificial Sequence
<220> FEATURE:
<223> OTHER INFORMATION: Primer

<400> SEQUENCE: 83
aagcagacta tgctgtctca ct                                               22

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
atcccgttgc ctttgttgac                                                  20

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
ggcaaaaggc tacagcagga                                                  20

<210> SEQ ID NO 86
<211> LENGTH: 20
<212> TYPE: DNA
<213> ORGANISM: Artificial Sequence
```

```
<220> FEATURE:
<223> OTHER INFORMATION: Primer

<400> SEQUENCE: 86
tcagggaagg cagaaatccc                                              20

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
tacgacgact acccggagaa                                              20

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
ggacgtccct ggagttcatc                                              20

<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
cagagagtgc cacgtgcata                                              20

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
tacgcttctt ggcggacttt                                              20

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
agaggtgtac cggcatttcg                                              20

<210> SEQ ID NO 92
<211> LENGTH: 20
<212> TYPE: DNA
<213> ORGANISM: Artificial Sequence
<220> FEATURE:
<223> OTHER INFORMATION: Primer

<400> SEQUENCE: 92
gtagggtttg gtgtggctgt                                              20
```

<210> SEQ ID NO 93
<211> LENGTH: 21
<212> TYPE: DNA
<213> ORGANISM: Artificial Sequence
<220> FEATURE:
<223> OTHER INFORMATION: Primer

<400> SEQUENCE: 93
accggctcaa caaggttatc a                                             21

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
ctgggcaatg acgtcttcaa                                               20

<210> SEQ ID NO 95
<211> LENGTH: 20
<212> TYPE: DNA
<213> ORGANISM: Artificial Sequence
<220> FEATURE:
<223> OTHER INFORMATION: Primer

<400> SEQUENCE: 95
tcctgatccc tttcccatcg                                               20

<210> SEQ ID NO 96
<211> LENGTH: 20
<212> TYPE: DNA
<213> ORGANISM: Artificial Sequence
<220> FEATURE:
<223> OTHER INFORMATION: Primer

<400> SEQUENCE: 96
tcctcctttt acgaccacca                                               20

<210> SEQ ID NO 97
<211> LENGTH: 21
<212> TYPE: DNA
<213> ORGANISM: Artificial Sequence
<220> FEATURE:
<223> OTHER INFORMATION: Primer

<400> SEQUENCE: 97
cttgtcctgg tgtgctagag t                                             21

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
cccccaccag tgaatcaaga                                               20